United States Patent
Tan et al.

(10) Patent No.: US 11,253,507 B2
(45) Date of Patent: Feb. 22, 2022

(54) COMPOSITION AND METHOD FOR PREVENTING OR DELAYING ONSET OF MYOPIA COMPRISING ATROPINE

(71) Applicant: Singapore Health Services PTE LTD, Singapore (SG)

(72) Inventors: Donald Tiang Hwee Tan, Singapore (SG); Audrey Chia, Singapore (SG); Roger Beuerman, Singapore (SG); Amutha Barathi Veluchamy, Singapore (SG)

(73) Assignee: Singapore Health Services Ptd Ltd, Singapore (SG)

( * ) Notice: Subject to any disclaimer, the term of this patent is extended or adjusted under 35 U.S.C. 154(b) by 0 days.

(21) Appl. No.: 16/487,423

(22) PCT Filed: Feb. 20, 2018

(86) PCT No.: PCT/IB2018/051039
§ 371 (c)(1),
(2) Date: Aug. 20, 2019

(87) PCT Pub. No.: WO2018/154440
PCT Pub. Date: Aug. 30, 2018

(65) Prior Publication Data
US 2020/0138801 A1    May 7, 2020

Related U.S. Application Data

(60) Provisional application No. 62/461,723, filed on Feb. 21, 2017.

(51) Int. Cl.
*A61K 31/46* (2006.01)
*A61P 27/10* (2006.01)
(Continued)

(52) U.S. Cl.
CPC ............ *A61K 31/46* (2013.01); *A61K 9/0048* (2013.01); *A61K 47/186* (2013.01); *A61K 47/38* (2013.01); *A61P 27/10* (2018.01)

(58) Field of Classification Search
CPC ........ A61K 31/46; A61K 9/0048; A61P 27/10
(Continued)

(56) References Cited

U.S. PATENT DOCUMENTS 9,421,199 B2 *  8/2016  Ostrow .................. A61K 47/02

FOREIGN PATENT DOCUMENTS

| WO | 2012/161655 A1 | 11/2012 |
| WO | 2016/172712 A2 | 10/2016 |
| WO | 2017/204262 A1 | 11/2017 |

OTHER PUBLICATIONS

Zhang et al, Experimental and Therapeutic Medicine, 2015, vol. 9. pp. 2420-2428. (Year: 2015).*

(Continued)

*Primary Examiner* — Craig D Ricci
*Assistant Examiner* — Janet L Coppins
(74) *Attorney, Agent, or Firm* — Kilpatrick Townsend & Stockton LLP

(57) ABSTRACT

Methods of preventing or delaying onset of myopia in pre-myopic patients and also methods of reducing or preventing progression of myopia in patients having low myopia through the use of compositions comprising less than 0.025% of atropine are disclosed.

20 Claims, 3 Drawing Sheets

(51) Int. Cl.
*A61K 9/00* (2006.01)
*A61K 47/18* (2017.01)
*A61K 47/38* (2006.01)

(58) Field of Classification Search
USPC .......................................................... 514/304
See application file for complete search history.

(56) References Cited

OTHER PUBLICATIONS

Web printout of https://www.reviewofoptometry.com/article/what-does-myopia-really-mean, "RO Staff" (Mar. 5, 2019). (Year: 2019).*
Chia A. et al, Five-Year Clinical Trial on Atropine for the Treatment of Myopia 2. Myopia Control with Atropine 0.01 % Eyedrops. Ophthalmology, Aug. 11, 2015, vol. 123, No. 2, pp. 391-399.
Chia A. et al., Atropine for the Treatment of Childhood Myopia: Changes after Stopping Atropine 0.01 %, 0.1 % and 0.5%. Am J Ophthalmol, Dec. 4, 2013, vol. 157, No. 2, pp. 451-457.
Clark T.Y. & Clark R.A., Atropine 0.01 % Eyedrops Significantly Reduce the Progression of Childhood Myopia. J Ocul Pharmacol Ther, Jul. 28, 2015, vol. 31, No. 9, pp. 541-545.
Loughman J. & Flitcroft D.I., The Acceptability and Visual Impact of 0.01 % Atropine in a Caucasian Population. Br J Ophthalmol, Feb. 22, 2016, vol. 100, No. 11, pp. 1525-1529.
Nishiyama Y. et al., Side Effects of Low Dose Atropine. Nippon Ganka Gakkai Zasshi, Nov. 1, 2015, vol. 119, No. 11, pp. 812-816.
Fang P.-C. et al., Prevention of Myopia Onset with 0.025% Atropine in Premyopic Children. J Ocul Pharmacol Ther, Aug. 1, 2010, vol. 26, No. 4, pp. 341-345.
Tan D. et al., Topical Atropine in the Control of Myopia. Asia Pac J Ophthalmol, Dec. 31, 2016, vol. 5, No. 6, pp. 424-428.
Ekdawi N.S. and Kipp M.A., Private practice experience with low-dose atropine for the treatment of progressive myopia. J AAPOS, Aug. 31, 2017, vol. 2 1, No. 4, p. e39.
PCT/IB2018/051039, "International Search Report and Written Opinion"; Jun. 7, 2018, 14 pages.
PCT/IB2018/051039, "International Preliminary Report on Patentability"; Sep. 6, 2019, 10 pages.

* cited by examiner

COMPOSITION AND METHOD FOR PREVENTING OR DELAYING ONSET OF MYOPIA COMPRISING ATROPINE

RELATED APPLICATIONS

This application claims the benefit of U.S. Provisional Application No. 62/461,723, filed Feb. 21, 2017. The entire contents of the foregoing provisional patent application is incorporated herein in its entirety for all purposes.

TECHNICAL FIELD

This application relates to methods of preventing or delaying the onset of myopia and methods of reducing or preventing the progression of myopia by administration of compositions comprising very low concentrations of atropine.

BACKGROUND

Myopia, otherwise known as, nearsightedness or short sightedness, is a type of refractive error of the eye, in which the visual image is focused in front of the retina, typically resulting in blurred vision of distant objects. Myopia is especially prevalent among Asians and has been reported to be as high as 70-90% in Asian countries. Myopia may be corrected by prescription lenses (for example, spectacles or contact lenses) or refractive surgery (for example, LASIK or phakic intraocular lens implantation).

Patients having a higher degree of myopia are at a higher risk of developing sight-threatening disorders such as degenerative retina changes such as peripheral lattice changes, tears and detachment, myopic choroidal neo-vascularization, myopic macular schisis and holes, posterior staphylomas, myopic macular degeneration, early-onset cataracts (in the 30s-40s), open angle glaucoma, and peri-papillary atrophy, optic disc tilt and pits. These disorders, if not properly treated, may result in visual loss later in life. Children with early onset myopia are more likely to eventually develop high myopia. A recent Singapore-based paper pooling data from the Singapore, Chinese, Indian and Malaysian adult studies showed that pathological symptoms of myopia, in particular staphyloma and chorioretinal atrophy, worsened with the progression of age, myopic refraction and axial length (Chang et al (2013)). As such, controlling the development and progression of myopia of a patient in childhood years, so that the eventual myopia is less than would have otherwise been (e.g., −5.00 D rather than −10.00 D), would have a major beneficial impact on the life of the patient.

BRIEF SUMMARY

This application relates to using compositions comprising very low concentration of atropine to prevent or delay onset of myopia, before myopia occurs, or preventing or reducing the progression of myopia.

In one aspect, this disclosure provides a method for preventing or delaying the onset of myopia comprising administering to a subject in an eye a composition comprising less than 0.025% atropine. In some embodiments, the atropine is present in the form of atropine sulphate. In some embodiments, composition comprises about 0.01% atropine. In some embodiments, wherein the composition comprises about 0.001% to 0.0249% atropine. In some embodiments, the composition comprising about 0.001%, 0.002%, 0.003%, 0.004%, 0.005%, 0.006%, 0.007%, 0.008%, 0.009%, 0.01%, 0.011%, 0.012%, 0.013%, 0.014%, 0.015%, 0.016%, 0.017%, 0.018%, 0.019%, 0.02%, 0.021%, 0.022%, 0.023%, 0.024%, 0.0245% or 0.0249% atropine. In some embodiments, the subject is 4 to 21 years old. In some embodiments, the subject is 5 to 9 years old. In some embodiments, the subject has pre-myopia.

In some embodiments, the composition is administered every other day, or at least once daily, or at least twice daily. In some embodiments, each administration is performed by instilling at least one drop, at least two drops, or at least three drops to the eye, wherein each drop contains about 20-100 microliter liquid. In some embodiments, the administration continues for the period of at least six months, one year, two years, three years, four years, five years, six years, seven years, ten years or longer.

In some embodiments, the composition further comprises at least one pharmaceutically acceptable excipient. In some embodiments, at least one pharmaceutically acceptable excipient is selected from the group consisting of benzalkonium chloride and hydroxypropyl methylcellulose. In some embodiments, benzalkonium chloride is present in the composition at a concentration of about 0.01%. In some embodiments, hydroxypropyl methylcellulose is present in the composition at a concentration of about 1%. In some embodiments, no preservative excipients are present in the composition.

In some embodiments, the Spherical Equivalent (SE) of the eye is within the range of from +1.00 D to −0.49 D before administration of the composition. In some embodiments, the SE is measured by Autorefractor after administration of cycloplegia.

In some embodiments, the subject has no astigmatism or has astigmatism of not more than 1.50 D as measured by cycloplegic or non-cycloplegic autorefraction before administration of the composition.

In some embodiments, the pupil of the eye has no dilation or a dilation of no greater than 2 mm, e.g., no greater than 1.9 mm, no greater than 1.8 mm, no greater than 1.7 mm, no greater than 1.5 mm, no greater than 1.49 mm during the period of administration of the composition. In some embodiments, the eye has no clinically significant loss of accommodation or experience a loss of accommodation of no greater than 10 D, e.g., no greater than 9 D, no greater than 8.5 D, no greater than 8.8 D, or no greater than 8 D. In some embodiments, the eye has no clinically significant loss of near visual acuity from loss of accommodation.

In some embodiments, wherein the onset of myopia is delayed for greater than 6 months, 12 months, 18 months, two years, three years, five years, six years, eight years, or longer.

In another aspect, this disclosure provides a method for reducing or preventing myopia progression comprising administering to a subject in an eye a composition comprising less than 0.025% atropine, wherein the composition is administered no more frequently than once every two days, once every three days, or once every four days. In some embodiments, each administration is performed by instilling at least one drop, at least two drops, or at least three drops to the eye, wherein each drop contains about 20-100 microliter liquid. In some embodiments, the SE of the eye is less than −1.50 D before administration of the composition. In some embodiments, the SE of the eye is within the range of from −0.50 D to −1.50 D before administration of the composition. In some embodiments, the subject is between 4 to 21 years old. In some embodiments, the subject is between 5 and 9 years old. In some embodiments, the atropine is present in the form of atropine sulphate. In some embodiments, the composition comprises about 0.001% to 0.0249% atropine, e.g., comprising about 0.001%, about 0.002%, about 0.003%, about 0.004%, about 0.005%, about 0.006%, about 0.007%, about 0.008%, about 0.009%, about 0.01%, about 0.011%, about 0.012%, about 0.013%, about 0.014%, about 0.015%, about 0.016%, about 0.017%, about 0.018%, about 0.019%, about 0.02%, about 0.021%, about 0.022%, about 0.023%, about 0.024%, about 0.0245% or about 0.0249% atropine. In some embodiments, the composition further comprises at least one pharmaceutically acceptable excipient. In some embodiments, the at least one pharmaceutically acceptable excipient is selected from benzalkonium chloride and hydroxypropyl methylcellulose. In some embodiments, no preservative excipients are present in the composition.

In some embodiments, the mean change of SE during a two year period following the start of administration of the composition is reduced by at least 20% as compared to controls. In some embodiments, treating a patient, e.g., a patient having pre-myopia, reduces the change in refraction by at least 10%, at least 20%, at least 30%, or at least 40%, or at least 50%, e.g., at least 53% over a period of 2 weeks, 1 month, 2 months, 6 months, one year, two years or more from the initiation of the treatment. In some embodiments, treating the patient, e.g., a patient having pre-myopia, reduces the increase of Axial length by at least 10%, at least 15%, at least 20%, at least 30% over a period of 1 week, 2 weeks, 1 month, 2 months, 6 months, one year, two years or more from or more, from the initiation of the treatment. In some embodiments, treating the patient, e.g., a patient having pre-myopia, with the composition disclosed herein, can reduce change in refraction by at least 10%, at least 20%, at least 30%, or at least 40%, or at least 50%, e.g., at least 53%.

In some embodiments, administration of the atropine composition disclosed herein reduces the change in refraction (i.e., myopic refractive error shift) by at least 10%, e.g., at least 20%, at least 30%, or at least 40%, at least 50%, or at least 53% as compared to controls. In some embodiments, treating the patient, e.g., a patient having pre-myopia, with the composition disclosed herein reduces the rate of myopia progression or myopia shift by at least 10%, e.g., at least 20%, at least 30%, or at least 40%, at least 50%, or at least 53% after onset of myopia as compared to controls. In some embodiments, treating the patient with the composition disclosed herein increases the length of the time period from initiation of the treatment to onset of myopia by at least 10%, e.g., at least 20%, at least 30%, or at least 40%, at least 50%, or at least 53% as compared to controls.

In some embodiments, the pupil of the eye has no dilation or a dilation of no greater than 1.9 mm, no greater than 1.8 mm, no greater than 1.7 mm, no greater than 1.5 mm, no greater than 1.49 mm during the period of administration of the composition. In some embodiments, the eye has no loss of accommodation or a loss of accommodation of no greater than 10 D, e.g., no greater than 9 D, no greater than 8.5 D, no greater than 8.8 D, or no greater than 8 D.

Also provided in this disclosure is a use of atropine in the preparation of a composition for preventing or delaying the onset of myopia progression and the composition comprises less than 0.025% atropine.

Also provided in this disclosure is a use of atropine in the preparation of a composition for reducing or preventing myopia progression in a subject that has a SE of less than −1.50 D, wherein the composition comprises less than 0.025% atropine, wherein the composition is administered no more frequently than once every two days.

Also provided herein is a composition for use in a method of preventing or delaying the onset of myopia progression, wherein the composition comprises less than 0.025% atropine. In some embodiments the composition comprises 0.001% to 0.0249% atropine.

Also provided herein is a composition for use in a method of reducing or preventing myopia progression in a subject, wherein the composition comprises less than 0.025% atropin, wherein the composition is administered no more frequently than once every two days. In some embodiments, the subject has a SE of less than −1.50 D. In some embodiments, the subject has a SE of less than −0.50 D.

DETAILED DESCRIPTION

Figure 1A:
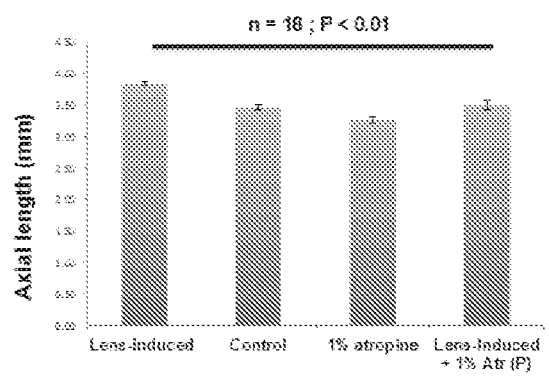
FIGS. 1A and 1B show effect of atropine treatment on axial elongation and refractive error, respectively.

Several studies on myopia control (preventing the progression of myopia) include the use of contact lenses, spectacles and pharmacological agents in the form of topical eye drops, mostly pertaining to the use of atropine or anti-muscarinic agents. All of these forms of myopia control therapy aim to slow down progression of myopia of children who have already become myopic.

Previously, Atropine in the Treatment Of Myopia study (ATOM) trials ATOM1 and ATOM2, involved young children between ages 6-12 old, who were already myopic, having SE of at least −2.00 D, and were progressing in myopic degree, prior to study recruitment. Various concentrations of atropine when administered at least once daily have been shown to effective in preventing or reducing progression in these myopic children. See, for example, WO 2012/161655.

However, no clinical trials to date have been performed to assess the feasibility of preventing the onset of myopia using very low concentration of atropine, before myopia occurs. No studies have been performed assessing the effect of using a composition comprising very low concentration atropine at no more frequently than every other day on progression of myopia.

The application is directed to using a composition comprising very low concentration of atropine to prevent or delay onset of myopia, before myopia occurs, and also using the composition no more frequently than once every two days, to reduce progression of myopia after the patient has already developed low myopia.

Definitions

Unless otherwise noted, all concentration unit refers to weight to volume. When a value of a parameter is referred as being within a range, the parameter's value can be the lower limit or higher limit, or any value in between.

Unless otherwise noted, whenever the language refer to that an SE value is greater or higher than a negative reference value, it means that the SE value is a negative value and the absolute value of which is greater than that of the negative reference value. For example, an SE value that is greater than −0.5 D can be −1.0 D.

Unless otherwise noted, whenever the language refers to an expression "A+/−B", A refers to the mean and B refers to the standard deviation ("SD"). For example, a dilation of 0.74+/−0.75 mm, refers to a mean dilation of 0.74 mm with a SD of 0.75.

The term "about" when used in conjunction with a value means any value that is reasonably close to the value, i.e., within the range of ±10% of the value. In particular, it would include the value itself. For example, both a value of 0.009% and a value of 0.011% are deemed to be "about 0.01%".

The term "myopia" refers to a patient's condition in which the patient has at least one eye with an SE value greater than −0.5 D, for example, −1.0 D, −2.0 D. Depending on context, "myopia" also refers to the condition of the eye, the SE value of which is higher than −0.5 D.

The term "pre-myopia" refers to a patient's condition in which the patient has at least one eye with an SE value within the range of −0.49 D to 1.00 D. Depending on context, myopic can also refer to the condition of the eye, the SE value of which is within the range of −0.49 D to 1.00 D.

The term "low myopia" refers to a patient's condition in which the patient has at least one eye with an SE value within the range of −0.50 D to −1.50 D. Depending on context, "low myopia" can also refer to the condition of the eye, the SE value of which is within the range of −0.50 D to −1.50 D.

The term "high myopia" refers to a person having at least one eye with an SE value that is greater than −5.0 D. Depending on context, "high myopia" can also refer to the condition of the eye, the SE value of which is greater than −5.0 D.

The term "drop" refers to the a unit of measure of volume, which is equal to the amount dispensed as one drop from a dropper or drip chamber to the eye. Typically, a drop contains 20-100 microliter liquid. In some cases, a drop contains between 30 microliter to 70 microliter, e.g., about 50 microliter liquid.

The term "patient" or the term "subject", used interchangeably in this disclosure, refers to any individual, regardless of the status of myopia. In some embodiments, the patient is a child between 5 and 12 years old, e.g., between 5 and 9 years old. In some embodiments, the patient is a child between 5 and 9 years old who has pre-myopia.

The term "atropine composition" refers to a composition comprising atropine or an atropine salt, e.g., atropine sulfate or atropine acetate. As such, in the case when atropine is present in the salt form, e.g., atropine sulfate, the concentrations of atropine referred to weight to volume concentration of the atropine salt in the atropine composition.

The term "unit dosage regimen," as used herein, refers to physically discrete units suitable as unitary dosages for human subjects, each unit containing a predetermined quantity of a compound (e.g., atropine, as described herein) or compounds, calculated in an amount sufficient to produce the desired treatment effect. In some cases, the compound, e.g., atropine, is present in each unit in association with a pharmaceutically acceptable diluent, carrier or vehicle. In some cases, each unit contains no preservatives.

Myopia

Refractive errors refer to conditions in which the eye does not bend light correctly, resulting in a blurred image. The main types of refractive errors include myopia (nearsightedness), hyperopia (farsightedness), presbyopia (loss of near vision with age), and astigmatism. Myopia is associated with axial elongation, which results in the eye ball being elongated and/or the cornea becomes too curved. As axial elongation progresses, the eyeball may become too long or the cornea (the clear front cover of the eye) is too curved, and as a result, the light entering the eye is not focused correctly, and distant objects look blurred. Myopia is also dependent on cornea curvature and lens power. Although myopia can develop at any age, typically the onset of myopia occurs during the grade school years and progresses until growth of the eye is completed.

Myopia is commonly assessed using spherical equivalent (SE) in ophthalmology clinics. The spherical equivalent is a single number in dioptres, and may be defined as a spherical power whose focal point coincides with the circle of least confusion of a spherocylindrical lens. SE is determined based on the values of sphere and cylinder of the eye and commonly expressed as the sum of the sphere value and one half of the cylinder value. The spherical equivalent is thus a convenient clinical method of representing data from several sources regarding refractive power. As myopia progresses, the refractive power changes into a negative value—a refractive error develops—, the axial length increases, and the absolute value of SE increases (the SE changes into a more negative value). Myopia occurs as a result of failure of the normal process of emmetropization, which is essentially endogenous to the eye. There is a mismatch between the focal length and the axial length of the eye, with the latter being too long for the refractive power of the lens and cornea. So, as myopia progresses, there is a shift in refractive power from hyperopic to myopic. In animal studies, myopia is typically assessed by measuring this refractive power (i.e., refractive error) in diopters and also measuring the axial length elongation. A diopter is a unit of refractive power that is equal to the reciprocal of the focal length (in meters) of a given lens. Refractive error change was recorded in diopters for animal studies as with spherical equivalent in the ophthalmology clinic.

Myopic patients have at least one eye the Spherical Equivalent ("SE") of which is −0.5 D or higher, e.g., −2.0 D or higher. The higher the absolute SE value, the higher degree of myopia. Patients do not have myopia typically have a positive SE value or a negative SE value less than −0.5 D.

Patients

In one aspect, the disclosure provides methods for preventing or delaying the onset of myopia by administering to a subject a composition comprising a very low concentration of atropine. For this aspect of the invention, the subjects are not myopic before the atropine treatment, i.e., the SE of the eye is a positive value or a negative value less than −0.5 D. In some embodiments, the subject is at a pre-myopic stage before being treated with atropine and they have a SE value within the range of +1.00 D to −0.49 D, e.g., 0.80 D to −0.49 D, or 0.50 D to −0.40 D.

In another aspect, the disclosure provides methods for reducing or preventing myopia progression in a subject comprising administering a composition comprising very low concentration of atropine, which is administered to the patient no more frequently than once every two days. In some cases, the subject has low myopia, i.e., having a negative SE value higher than −0.5 D but less than −1.50 D.

A patient who can benefit from atropine treatments as disclosed herein can be of any age group. In some embodiments, the patient is at least 5 years old. In preferred embodiments, the patient is a child at an age that is within the range of 5-17, e.g., 5-12, e.g., 5-9 years old. In some cases, the patient is at an age that is within the range of 5-6 years or 7-9 years old. In some cases, the patient has no history of cardiac or significant respiratory illness. In some cases, the patient has distance vision correctable to logMAR0.2 or better in both eyes determined by the log Mar vision chart. In some cases, the subjects have normal intraocular pressure of not greater than 21 mmHg as determined by tonometry. In some cases, the subject has at least one parent who is myopic. In some cases, the patient has normal ocular health other than being myopic or pre-myopic.

Methods that can be used to determine the ocular health of a patient are well known. Non-limiting exemplar methods include slit lamp examination, fundus photography, Intraocular lens (IOL) Master biometry, and/or cycloplegic autorefraction/autokeratometry. In some cases, two, three or all of the aforementioned methods are performed to evaluate the patient's ocular health, including assessing the degree of myopia by determining SE values.

Atropine

Atropine is a non-selective muscarinic antagonist, which degrades slowly, typically wearing off in 7 to 14 days. Currently, atropine is used as a cycloplegic to temporarily paralyze the accommodation reflex to dilate the pupils. Atropine can also be used to treat a number of disease related to eye, such as uveitis and early amblyopia, and has been used previously for treating patients already have moderate to high myopia, i.e., having a negative SE value of higher than −2.00 D. In both human and mouse, atropine can bind to five types of muscarinic receptors that are primarily present in the fibroblasts of the sclera. These sclera fibroblasts are responsible for controlling the sclera growth.

Throughout the disclosure, the term "accommodation amplitude", used interchangeably with the term "accommodation", refers to the ability of the eye to focus on near objects. Atropine can cause systemic as well as local side effects such as pupil dilation and a decrease of accommodation amplitude. An increase in pupil size would result in an exponential increase in the amount of light entering the eye and may cause glare and photophobia. Excessive amounts of ultraviolet light entering an eye may increase the risk of cataract or macular degeneration. A decrease in accommodation amplitude may reduce near vision such that children affected by this need bifocal or progressive glasses to read or see close objects.

This disclosure provides methods of preventing or delaying the onset of myopia by administering to the eye a composition comprising a very low concentration of atropine. Also provided are methods of reducing or preventing the progression of myopia by administering the low concentrations of atropine in a low frequency, i.e. no more frequently than once every two days. The composition typically comprises less than 0.025% atropine, e.g., about 0.001% to about 0.0249% atropine, about 0.005% to about 0.002%, about 0.008% to about 0.015%, e.g., about 0.009% to about 0.012%. In particular embodiments, the composition comprises about 0.01% atropine. In some embodiments, the composition comprises about 0.001%, about 0.002%, about 0.003%, about 0.004%, about 0.005%, about 0.006%, about 0.007%, about 0.008%, about 0.009%, about 0.01%, about 0.011%, about 0.012%, about 0.013%, about 0.014%, about 0.015%, about 0.016%, about 0.017%, about 0.018%, about 0.019%, about 0.02%, about 0.021%, about 0.022%, about 0.023%, about 0.024%, about 0.0245% or about 0.0249% atropine. In some embodiments, atropine in the composition is present as a salt, e.g., atropine sulfate.

In some embodiments, treating the patient with the composition disclosed herein can delay the onset of myopia for greater than 1 month, greater than 3 months, greater than 4 months, greater than 5 months, greater than 6 months, greater than 12 months, greater than 18 months, greater than two years, greater than three years, greater than five years, greater than six years, or greater than eight years as compared to controls. For purpose of this disclosure, controls refer to individuals who are not treated with the atropine composition disclosed herein. In preferred embodiments, the individuals in the control group are from the same age group and at the same premyopic or myopic stage as the individuals who are treated with the compositions disclosed herein.

In some embodiments, treating the patient, e.g., a patient having pre-myopia, with the composition disclosed herein can reduce the increase of Axial length (the length of the axis from the center of the cornea to where the image is most clear on retina) by at least 10%, at least 15%, at least 20%, at least 30% over a period of one week to eight years, e.g., one month to five years, four months to four years, six months to three years, or one year to two years from the initiation of the treatment.

In some embodiments, treating the patient, e.g., a patient having pre-myopia, with the composition disclosed herein, can reduce change in refraction (i.e., myopic refractive error shift) by at least 10%, e.g., at least 20%, at least 30%, or at least 40%, at least 50%, or at least 53% as compared to controls. In some embodiments, treating the patient, e.g., a patient having pre-myopia, with the composition disclosed herein can reduce the rate of myopia progression or myopia shift by at least 10%, e.g., at least 20%, at least 30%, or at least 40%, at least 50%, or at least 53% after onset of myopia as compared to controls. In some embodiments, treating the patient with the composition disclosed herein can increase the length of the time period from initiation of the treatment to onset of myopia by at least 10%, e.g., at least 20%, at least 30%, or at least 40%, at least 50%, or at least 53% as compared to controls.

Pharmaceutical Compositions

In some embodiments, the present invention provides a pharmaceutical composition including a pharmaceutically acceptable excipient and atropine and the method of administering the composition for preventing or delaying the onset of myopia or reducing or preventing progression of myopia.

The pharmaceutically acceptable excipients include carbohydrate or protein fillers include, but are not limited to sugars, including lactose, sucrose, mannitol, or sorbitol; starch from corn, wheat, rice, potato, or other plants; cellulose such as methyl cellulose, hydroxypropyl methylcellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate. In some embodiments, the pharmaceutically acceptable excipient comprises benzalkonium chloride, at a concentration within the range of 0.005% to 0.02%, e.g., about 0.01%. In some embodiments, the pharmaceutically acceptable excipient comprises hydroxypropyl methylcellulose at a concentration within the range of 0.5% to 2%, e.g., about 1%. In some embodiments, the pharmaceutically acceptable excipient comprises both hydroxypropyl methylcellulose and Benzalkonium Chloride.

In some embodiments, the atropine composition is prepared in liquid form for eye administration. Details on techniques for formulation and administration are well described in the scientific and patent literature, see, e.g., the latest edition of Remington's Pharmaceutical Sciences, Maack Publishing Co, Easton, Pa. ("Remington's").

Liquid form preparations include solutions, suspensions, and emulsions, for example, water or water/propylene glycol solutions. Solutions suitable for eye administration can be prepared by dissolving the active component in water and adding suitable colorants, stabilizers, buffers, dispersants, solubilizing agents, preservatives, and/or thickening agents as desired. In some embodiments, the solution can be made by dispersing the finely divided atropine in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate or benzalkonium chloride.

The pharmaceutical compositions can be packaged in unit dose regimen. This can reduce administration error and contamination. In some embodiments, the pharmaceutical composition is a preservative-free composition in a unit dose regimen.

Also included are solid form preparations, which are intended to be converted, shortly before use, to liquid form preparations for eye administration. Solid form preparations include powders, tablets, pills, capsules, cachets, suppositories, and dispersible granules. A solid carrier can be one or more substances, which may also act as diluents, binders, preservatives, tablet disintegrating agents, or an encapsulating material.

The pharmaceutical formulations of the disclosure can be provided as a salt and can be formed with many acids, including but not limited to sulfuric, hydrochloric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, and the lyophilized powder is combined with buffer prior to use.

The pharmaceutical preparation is preferably in unit dosage form. In such form the preparation is subdivided into unit doses containing appropriate quantities of the active component, atropine. The unit dosage form can be a packaged preparation, the package containing discrete quantities of preparation, such as packeted tablets, capsules, and powders or solutions in droppers, vials or ampoules.

Administration

The atropine composition disclosed herein can be delivered to the eye via a topical route, formulated as solutions, suspensions, emulsions, gels, ointments, pastes, etc. In some cases, the atropine composition is formulated as a solution to be applied, one drop per eye for each administration. Typically, one drop has a volume of between 20 µL and 100 µL, e.g., 25 µL-60 µL, e.g., 50 µL. The atropine composition can be administered any time during the 24 hours in a day. In some cases, the atropine solution is administered to these patients once, twice, or more times per day to prevent or delay the onset of myopia in patients; especially those are at a pre-myopic stage. In some cases, the atropine solution is applied every two days, every three days, or every four days to reduce or prevent progression of myopia in patient, especially those who have low myopia. In some cases, each administration is performed by instilling at least one drop, at least two drops, or at least three drops to the eye, wherein each drop contains about 20-100 microliter liquid.

The duration of treatment with atropine to treat patients, e.g., children having pre-myopia or low myopia, can vary according to severity of the condition in a subject and the subject's response to atropine. In general, the composition disclosed herein, comprising very low concentration of atropine, e.g., about 0.01%, can be administered for a very long term and without causing clinically-significant adverse effects. Treatment with the atropine in accordance with the invention thus may last for as long as five, six, eight, ten years or even longer. In some embodiments, the composition can be administered for a period of about 4 weeks to 10 years, more typically about 6 weeks to about 5 years, most typically about 1 year to 2 years. Suitable periods of administration also include about 6 months to about 1 year, 18 months to 2 years, 9 to 16 months, 16 to 24 months, 16 to 32 months, 24 to 32 months, 24 to 48 months, 32 to 48 months, 32 to 52 months, 48 to 52 months, 48 to 64 months, 52 to 64 months, 52 to 72 months, 64 to 72 months, 64 to 80 months, 72 to 80 months, 72 to 88 months, 80 to 88 months, 80 to 96 months, 88 to 96 months, and 96 to 104 months. Suitable periods of administration also include 5, 6, 7, 8, 9, 10, 11, 12, 13, 14, 15, 16, 17, 18, 19, 20, 24, 25, 30, 32, 35, 40, 45, 48, and 50 months. Generally administration of the atropine composition should be continued until clinically significant improvement of the condition is observed.

In some embodiments, administration of an atropine composition is not continuous and can be stopped for one or more periods of time, followed by one or more periods of time where administration resumes. Suitable periods where administration stops include 5 to 9 months, 5 to 16 months, 9 to 16 months, 16 to 24 months, 16 to 32 months, 24 to 32 months, 24 to 48 months, 32 to 48 months, 32 to 52 months, 48 to 52 months, 48 to 64 months, 52 to 64 months, 52 to 72 months, 64 to 72 months, 64 to 80 months, 72 to 80 months, 72 to 88 months, 80 to 88 months, 80 to 96 months, 88 to 96 months, and 96 to 100 months. Suitable periods where administration stops also include 5, 6, 7, 8, 9, 10, 11, 12, 13, 14, 15, 16, 17, 18, 19, 20, 24, 25, 30, 32, 35, 40, 45, 48 50, 52, 55, 60, 64, 65, 68, 70, 72, 75, 80, 85, 88 90, 95, 96, and 100 months.

The atropine composition disclosed herein can be used in combination with other active agents known to be useful for preventing onset or progression of myopia, or with adjunctive agents that may not be effective alone, but may contribute to the efficacy of atropine.

An atropine composition can be placed in an appropriate container, such as bottles or droppers, and labeled for treatment of an indicated condition. For administration of the atropine composition, such labeling would include, e.g., instructions concerning the amount, frequency and method of administration.

The atropine composition can also be prepared into unit doses containing appropriate quantities of the active component, atropine. The unit dosage regimen can be a packaged preparation, the package containing discrete quantities of preparation, such as packeted tablets, capsules, and powders or solutions in droppers, vials or ampoules.

Determining the Effects of Atropine

This disclosure provides a method of preventing or delaying the onset of myopia to subjects having no myopia before being treated. Atropine's effect on preventing or delaying the onset of myopia can be assessed by examining the eye during periodic, scheduled visits during treatment and determining the timing when the patient first becomes myopic, i.e., when the patient's SE reaches about −0.5 D or slightly above. The timing is then compared with the timing of the onset of myopia in a control group who does not receive atropine treatment, but will receive vehicle placebo eye drops. The control subject is typically of age and ethnic background that is the same as or very similar to the patient treated with atropine. The subjects in the control group may also have ocular health status comparable to that of the individuals in the treatment group before the beginning of atropine treatment. In preferred embodiments, the individuals from the control group are pre-myopic and between ages of 5 and 9. Ocular health of these individuals can be determined using the methods above and may include one or more of the following: measuring distance and near logMar visual acuity, performing non-cyclopletic autorefraction/autokerametry, performing cover tests, performing lensometry, measuring photopic pupil diameter, and measuring amplitude of accommodation. In some embodiments, the data related to timing of onset of myopia of a control are average historical patient data in existing clinical databases.

Patients selected for treatment are monitored for ocular health at the beginning of the treatment and during periodic examinations during and/or after treatment. In some cases, the patients are monitored, e.g., every four, five, six months, seven, or eight months during and/or after the treatment period. In some cases, patients are examined for ocular health, including the degree of myopia at the 6th, 12th, 18th, 24th, and 30th month after treatment begins. Parameters that can be used to determine SE are also recorded at each visit and SE values are determined afterwards.

Pre-myopic subjects, e.g., children between the ages of 5 and 9, who do not receive any treatment, typically develop myopia within 6 to 12 months. Treating patients with the composition disclosed herein can prevent or delay the onset of myopia. Typically, the composition comprises less than 0.025% atropine, e.g., about 0.001% to 0.0249% atropine. In particular embodiments, the composition comprises about 0.01% atropine. In some embodiments, the composition comprises about 0.001%, about 0.002%, about 0.003%, about 0.004%, about 0.005%, about 0.006%, about 0.007%, about 0.008%, about 0.009%, about 0.01%, about 0.011%, about 0.012%, about 0.013%, about 0.014%, about 0.015%, about 0.016%, about 0.017%, about 0.018%, about 0.019%, about 0.02%, about 0.021%, about 0.022%, about 0.023%, about 0.024%, about 0.0245% or about 0.0249% atropine. In some embodiments, atropine in the composition is present as a salt, e.g., atropine sulfate. In some cases, the patient does not develop myopia until after two years, after three years after being diagnosed as having pre-myopia. In some cases, the onset of myopia is delayed for greater than 6 months, 12 months, 18 months, two years, three years, five years, six years, eight years, or longer as compared to controls.

The disclosure also provides a method of reducing or preventing the progression of myopia using the atropine compositions disclosed above. In some cases, these patients have already been diagnosed as having low myopia. As with assessing the composition's effect on preventing or delaying the onset of myopia, the effect on preventing or delaying progression of myopia can also be evaluated by monitoring the patients periodically before, during, and/or after the atropine treatment period. Ocular health parameters are obtained during these examinations and SE values are determined and are compared with SEs in controls over the same length of period of time. In some cases, no change in SE is observed during and after the treatment with the composition comprising very low concentrations atropine, indicating the atropine treatment prevents the progression of myopia. In some case, myopia still progresses and the negative SE values continue to increase, but the increase is smaller as compared to the increase in SE in the controls, indicating that the progression of myopia is reduced. In some embodiments, the atropine treatment over a period of time can reduce the mean change of SE by at least 20%, at least 30%, at least 40%, at least 50%, at least 60%, at least 80% as compared to controls over the same length of period of time. In some cases, the period is six months, one year, two years, three years, five years, or six years, or longer.

The compositions disclosed herein comprise very low concentrations of atropine, e.g., less than 0.025%, e.g., 0.01%, and they do not cause significant, adverse effects, such as pupil dilation and/or accommodation loss. The pupil dilation associated with the treatment is often no greater than 2 mm, e.g., no greater than 1.9 mm, no greater than 1.8 mm, no greater than 1.7 mm, no greater than 1.5 mm, or no greater than 1.49 mm. Typically, patients treated with the composition disclosed above may experience pupil dilation of 0.74+/−0.75 mm. The loss of accommodation associated with the treatment is also minimal, typically no greater than 10 D, e.g., no greater than 9 D, no greater than 8.5 D, no greater than 8.8 D, or no greater than 8 D. Typically, patents treated with the composition disclosed above may experience a loss of accommodation of 4.6+/−4.2 D.

EXAMPLES

The following examples are for illustrative purposes only and should not be interpreted as limitations of the claimed invention. There are a variety of alternative techniques and procedures available to those of skill in the art which would similarly permit one to successfully perform the intended invention.

Example 1

Inducing Form Deprivation Myopia in Mouse

Mouse is a good preclinical model to evaluate pharmacological treatments for myopia since the mouse eye has a very similar structure and biochemistry as the human eye, and previous studies have confirmed of the mouse model of myopia. The mouse eye also has pharmacological targets similar to those in the human eye. The results showed that Atropine given topically prior to the eye experiencing a procedure to induce myopia can avert some or all of the myopic changes. It has been shown that the relevant all of muscarinic receptor types in the fibroblasts of the tough outer connective tissue coating of the eye, the sclera are similar for the mouse eye and the human eye.

In general, form deprivation myopia ("FDM") in the mouse can be reliably created by attaching a −10 D lens over the mouse eye for 6 weeks. This causes an increase in axial length and refractive error of the mouse eye. In this procedure, the eyes will be treated with atropine once daily for 1-14 days prior to placing the −10 D lens over the eye. Initial experimental groups (n=8/group) will include: a) atropine treatment starting day 21 without lens placement and continuing for four weeks; b) −10 D lens placement at day 35 after two weeks of atropine treatment and continuing lens treatment for 4 weeks; c) −10 D lens placement at day 35 after one week of atropine treatment and continuing lens treatment for 4 weeks; d) −10 D lens placement at day 35 without prior atropine treatment and continuing for 4 weeks; e) control without lens or atropine.

After experimental treatment begins, the mice will be monitored every two weeks for axial length and refractive error changes using procedures as previously published. Refractions and biometry measurements will be carried out every two weeks. Axial length is measured with the in vivo Optic Low Coherence Interferometry (OLCI-AcMaster). Refraction is measured by automated eccentric photorefractor. Details of the methods have been previously described (Barathi V A & Beuerman R W, 2011; Barathi et al 2013).

Example 2

Effect of Atropine Eye Drops Prior to Inducing Form Deprivation Myopia in a Mouse Model Methods:

Animals: Breeding pair B6J (Mus musculus) mice were obtained from Jackson Lab and produced offspring. Naive control animals were housed in groups of 6 while experimental animals were housed individually in standard mouse cages after 21 days of age at 25° C. on a schedule of 12:12 h of light on and off with mouse pellets and water available ad libidum. Approval was obtained from the SingHealth Institutional Animal Care and Use of Committee (IACUC) and all procedures performed in this study complied with the Association of Research in Vision and Ophthalmology (ARVO) Statement for the Use of Animals in Ophthalmology and Vision Research.

Murine Myopia Model: A −10 D contact lens (PMMA Contact Lens in Grey Tint, 8.5 mm diameter, 8 mm base curve, refractive Index: 1.43, axial thickness: 0.5 mm) was placed over the right eye on day 21 by gluing to an annulus of velcro, and then attaching to a matching piece of velcro that had been previously sutured to the skin around the eye. The spectacle lenses were cleaned daily in dim light and left eyes were uncovered and served as controls. All optical appliances were removed on postnatal day 63.

Treatment Protocols:

Delayed FDM was induced in four groups of mice: groups 1-4. Group 1 (n=6, 3 batch) received a daily 10 μl of 1% topical application of atropine sulfate (ATG) on day 35 for 4 weeks, and Group 2 (n=6, 3 batch) received daily 10 μl of 1% topical application of atropine sulfate (ATG) on day 21 for 2 weeks and then −10 D lens was applied to induce myopia (pATG+LIM) for 4 weeks, Group 3 (n=6, 3 batch) was treated with the −10 D lens alone to induce myopia (lens applied on day 21 and continued for 6 weeks), Group 4 (n=3 [both eyes are naïve control], 3 batch) was used as naïve control. The right eye was used as an experimental and left eye was served as a contra-lateral control in all groups. Noting that experimentally-induced myopia in mice has been consistently found to have contralateral effects both for induction and drug intervention.

Ocular biometry assessment: Refractions and biometry measurements were recorded every week until the end of the study. Axial length was measured with in vivo Optic Low Coherence Interferometry (OLCI-AcMaster). Refraction was measured by automated eccentric photorefractor. Details of the methods were previously described (Barathi V et al., 2013; Barathi V A & Beuerman R W, 2011).

Statistical analysis: Statistical analysis was performed using SPSS software (Version11.0, Chicago, 145 USA). The results were expressed with mean±standard error (SEM). All values for the lens-induced eyes were statistically compared with those of the fellow eyes within the same group using a paired sample t-test. The mean interocular difference was used for an independent sample t-test between the experimental and normal groups. Statistical analysis among groups was performed by one-way analysis of variance (ANOVA), and statistical significance was considered when P<0.05.

Figure 1B:
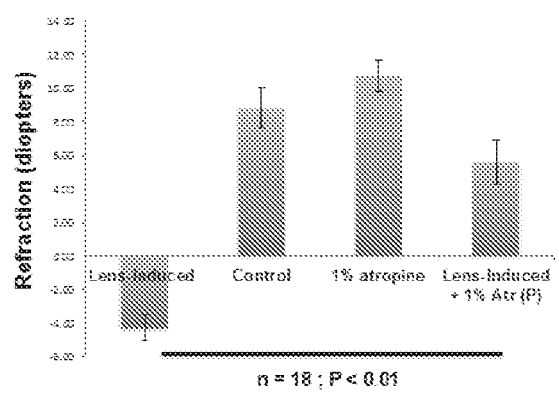

Results:

Atropine treatment with delayed induction of myopia is effective in diminishing the effect on axial length and refraction that would otherwise be expected. Eyes receiving atropine sulfate for 2 weeks prior to induction of myopia (−10 D lens for 4 weeks) remained hyperopic (FIG. 1B, p<0.01). However, this was significantly different when compared to −10 D lens treatment without prior atropine. Additionally, these results were less hyperopic as compared to 1% atropine treated eyes. This result indicates that the atropine pretreatment reduces the progression of myopia.

Atropine treatment reduced axial elongation: Spectacle lens induction for a period of 35 days resulted in statistically significant axial elongation (FIG. 1A, p<0.01, n=18) when compared to the contra-lateral control eyes.

Daily application of atropine as prevention for induced myopia, Group 2, at a concentration of 1%, blocked most of the elongation of axial length, with spectacle-lens induced myopia (FIG. 1A, p<0.01, n=18), but did not significantly affect the rate of axial elongation as compared to daily application of 1% atropine received eyes (p=0.114). The naive control and contra-lateral control eye biometry measurements were not significantly different.

Refractive error changes with atropine treatment: Eyes wearing −10 D lens alone, the refraction was shifted from hyperopic to myopic (FIG. 1B, p<0.01, n=18 as compared to contra-lateral control) after 6 weeks of induction. Eyes received atropine sulfate for 2 weeks prior to induce myopia (wearing −10 D lens for 4 weeks) were hyperopic (FIG. 1B, p<0.01) and significantly different when compared to −10 D lens treatment. However, this was less hyperopic as compared to 1% atropine treated eyes. This result indicates that the atropine prevention treatment reduces the progression of myopia.

There was no significant difference seen in the contra-lateral control eyes as compared to naïve control eyes.

Example 3

Effect of 0.01% Atropine in Mouse Model

Methods

Animals: Three weeks old C57BL/6J mice were purchased from InVivos, Singapore and were held at the animal holding unit of SingHealth Experimental Medicine Centre. The experimental animals were housed individually in standard mouse cages at 25° C. on a schedule of 12:12 h of light on (325 lx) and off (0 lx), with mouse pellets and water available ad libidum. All the procedures performed in this study complied with the Association of Research in Vision and Ophthalmology (ARVO) Statement for the Use of Animals in Ophthalmic and Vision Research and were approved by SingHealth IACUC. Both the eyes of each animal were screened for the ophthalmic abnormalities, such as corneal opacities and anterior polar cataracts. Animals with any form of ophthalmic abnormality were removed from the study (around 10%).

Mouse model of experimental myopia: Spectacle lens-induced myopia model was established by placing −15 D hard lens on the right eye of the animal, which served as the experimental eye, at post-natal day 35. Briefly, a −15 D lens (PMMA spectacle lens in blue tint, radius of outer curvature 8.5, inner curvature 8 mm, lens thickness 0.5 mm, Flexilens, India) was glued to an annulus (with 8 mm base curve) of Velcro. This mating piece was then attached to the Velcro that had been previously glued to the hair around the right experimental eye using a cyanoacrylate (Super Glue gel, UHU, Germany). This set up ensures that an air gap of 1.5 mm existed between the back part of the lens and the anterior surface of the cornea, so that the contact lens optically acted as a spectacle lens. The right eye of naïve group was attached with plano lens and acted as a negative control in the experimental study. Both the eyes in each animal were examined daily for any infection and the lenses were also cleaned regularly in dim red light. Left eyes were kept uncovered and were not used for any ocular biometry measurement in this study. Elizabethan collars made from thin plastic were fitted around the neck of each mouse upon lens-induction. This was done so as to prevent the mice from removing their lenses. Food pellets were placed on the floor of the cage to make eating easier. This strategy has also been followed previously by other groups doing mouse model of lens-induced myopia (Schaeffel et al., 2004).

Treatment protocols: A total of 27 mice were divided into 4 different groups as mentioned in Table 1, below. Vehicle and 0.01% atropine treatment started at post-natal day 22 in groups 1 and 2 respectively and continued for 2 weeks till post-natal day 35. 7 µL of drug was administered topically to the right eye in dim red light at the same time each day. This was followed by lens (either −15 D or plano) induction on post-natal day 35, that was kept attached until day 49.

TABLE 1

Study design

| | Study Groups | N | Lens | |
|---|---|---|---|---|
| 1 | Vehicle with lens (−15D) | 7 | R | + |
| | | | L | − |
| 2 | 0.01% Atropine with lens (−15D) | 7 | R | + |
| | | | L | − |
| 3 | Lens only (−15D) | 7 | R | + |
| | | | L | − |
| 4 | Naïve (with plano lens) | 6 | R | + |
| | | | L | − |

Results

Figure 3A:
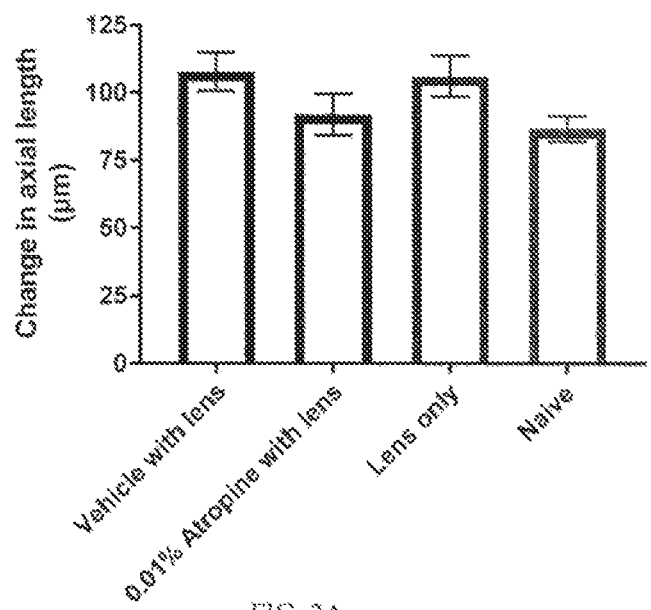
FIGS. 3A and 3B show the effect of pre-treatment with 0.01% atropine on ocular biometry in lens-induced myopia in C57BL/6J mice.
Figure 3B:
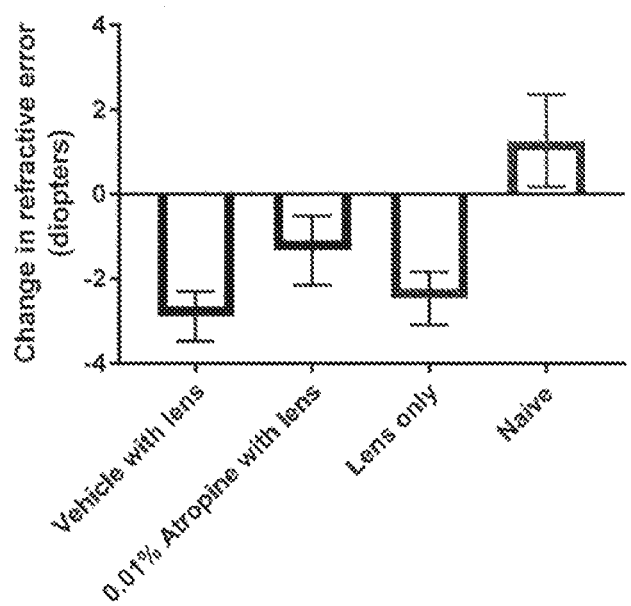

Ocular biometry such as axial length (AL) and refraction measurements were measured as described in Example 2. The measurements were done just before and 2 weeks after lens-induction, at days 35 and 49, respectively. See Table 2. The data was analyzed using the GraphPad Prism software version 7.02. Changes in AL and refraction between any two groups were analyzed using independent unpaired t-tests. A difference at p value<0.05 was considered statistically significant. Data are reported as mean+/−SEM. The body weights were recorded at post-natal days 22, 35 and 49. Neither the drug (atropine and vehicle) nor the lens treatment adversely impacted the body weights at any given time. Changes in AL and refraction at day 49 relative to measurements at day 35 are shown in FIG. 3A and FIG. 3B, respectively. The results, expressed as mean+/−SEM (n=6/7 per group), indicate that −15 D lens induction for a period of 2 weeks resulted in myopic refractive shift (a change from 1.22 D+/−0.89 to −2.97 D+/−0.44; two-tailed p-value=0.0083) and an increase in the AL of experimental eye by ~22% (from 0.087 mm+/−0.005 to 0.106 mm+/−0.008; two-tailed p-value=0.0606) with respect to the naïve group in mice. Topical administration of 0.01% atropine for 2 weeks before lens-induction reduced the increase in AL by ~15% in lens-induced myopic eyes as compared to the vehicle pre-treated myopic eyes in mice (a drop in the mean value of change in AL from 0.108 mm+/−0.007 in group 1 to 0.092 mm+/−0.008 in group 2; two-tailed p-value=0.1557). In addition, 0.01% atropine pre-treatment also induced a refractive shift from myopic to hyperopic after 2 weeks of ocular compensation to imposed defocus by −15 D lens (with changes in refraction measurements between post-natal days 35 and 49 being −2.89 D+/−0.59 and −1.33 D+/−0.82 in groups 1 and 2, respectively; two-tailed p-value=0.1483). Furthermore, vehicle treatment did not have any impact on ocular biometric changes in lens-induced myopia model (two-tailed p-values of 0.8712 and 0.6341 for changes in AL and refraction respectively). Taken together, these results suggest that pre-treatment with 0.01% atropine in growing eyes can minimize the development of lens-induced experimental myopia in mice.

TABLE 2

| Treatment | Cage ID# | Gender | AL at D35 (mm) | AL at D49 (mm) | Change in AL (mm) | Refraction at D35 (Diopter) | Refraction at D49 (Diopter) | Change in refraction (Diopter) |
|---|---|---|---|---|---|---|---|---|
| Group1 Vehicle with lens | 412 | M | 3.276 | 3.360 | 0.084 | 1.47 | −2.53 | −4.01 |
| | 413 | M | 3.284 | 3.412 | 0.128 | 4.77 | 0.36 | −4.41 |
| | 414 | M | 3.281 | 3.417 | 0.136 | 2.66 | 1.66 | −1.00 |
| | 416 | M | 3.263 | 3.359 | 0.097 | 6.70 | 4.80 | −1.90 |
| | 417 | M | 3.147 | 3.241 | 0.094 | 3.71 | 0.37 | −3.34 |
| | 418 | F | 3.207 | 3.312 | 0.105 | 1.66 | 0.63 | −1.02 |
| | 419 | F | 3.224 | 3.334 | 0.111 | 2.82 | −1.74 | −4.55 |
| Avg +/− SEM | | | | | 0.108 +/− 0.007 | | | −2.89 +/− 0.59 |
| Group2 0.01% Atropine with lens | 420 | F | 3.189 | 3.268 | 0.079 | 7.44 | 5.22 | −2.22 |
| | 421 | F | 3.159 | 3.238 | 0.079 | 3.71 | −1.85 | −5.57 |
| | 422 | F | 3.195 | 3.277 | 0.082 | 7.66 | 6.30 | −1.37 |
| | 423 | F | 3.214 | 3.340 | 0.126 | 5.96 | 6.26 | 0.30 |
| | 424 | M | 3.297 | 3.374 | 0.077 | 5.29 | 6.27 | 0.99 |
| | 425 | M | 3.250 | 3.335 | 0.084 | 5.43 | 4.17 | −1.26 |
| | 427 | M | 3.269 | 3.386 | 0.117 | 8.34 | 8.14 | −0.20 |
| Avg +/− SEM | | | | | 0.092 +/− 0.008 | | | −1.33 +/− 0.82 |
| Group3 Lens only | 428 | M | 3.285 | 3.363 | 0.078 | 5.33 | 3.42 | −1.92 |
| | 429 | M | 3.246 | 3.360 | 0.114 | 2.85 | 0.25 | −2.60 |
| | 430 | M | 3.256 | 3.343 | 0.087 | 5.45 | 2.14 | −3.31 |
| | 431 | F | 3.243 | 3.353 | 0.109 | 4.54 | 2.64 | −1.90 |

TABLE 2-continued

| Treatment | Cage ID# | Gender | AL at D35 (mm) | AL at D49 (mm) | Change in AL (mm) | Refraction at D35 (Diopter) | Refraction at D49 (Diopter) | Change in refraction (Diopter) |
|---|---|---|---|---|---|---|---|---|
| | 432 | F | 3.241 | 3.338 | 0.097 | 3.94 | 1.54 | −2.40 |
| | 434 | F | 3.249 | 3.383 | 0.134 | 6.50 | 1.30 | −5.20 |
| | 435 | F | 3.182 | 3.306 | 0.124 | 2.10 | −1.33 | −3.43 |
| Avg +/− SEM | | | | | 0.106 +/− 0.008 | | | −2.97 +/− 0.44 |
| Group4 Naïve | 436 | M | 3.278 | 3.359 | 0.081 | 6.52 | 7.54 | 1.02 |
| | 437 | M | 3.259 | 3.367 | 0.108 | 5.30 | 7.25 | 1.96 |
| | 438 | F | 3.253 | 3.337 | 0.084 | 2.74 | 5.76 | 3.02 |
| | 439 | F | 3.223 | 3.306 | 0.083 | 3.30 | 5.31 | 2.01 |
| | 442 | F | 3.199 | 3.273 | 0.074 | 4.05 | 1.01 | −3.04 |
| | 441 | F | 3.183 | 3.272 | 0.090 | 4.12 | 6.49 | 2.37 |
| Avg +/− SEM | | | | | 0.087 +/− 0.005 | | | 1.22 +/− 0.89 |

Example 4

Atom3 Study

1. Study Population 1.1 List the Number and Nature of Subjects To Be Enrolled

Eligible children, aged 5 to 9 years, 420 who are pre-myopic (SE −0.49 D to 1.00 D) and 150 who have low myopia (SE −0.50 D to −1.50 D). The pre-myopic children will be randomized to receive atropine 0.01% eye drops daily or placebo and the low myopic children will be randomized to receive either atropine 0.01% daily, atropine 0.01% alternate-day or placebo daily.

1.2 Criteria for Recruitment and Recruitment Process

Recruitment: The goal is to enrol 570 eligible children within the study period. Previously, the Singapore Eye Research Institute was able to recruit 400 myopia children in 1 year, but recruitment of younger and pre-myopic children may be more challenging. Standardized material (e.g., brochure and letters) describing the study will be developed and used by all investigators when communicating with the public about the study.

Recruitment strategies include engaging doctors in eye clinics (at the Singapore National Eye Centre), during eye forums, media releases, advertisements, letters to doctors, optometrist or opticians, letter to parents with myopia (e.g., in high myopia clinic).

1.3 Inclusion Criteria

Written Informed Consent from parent and assent from child has been obtained 5 to 9 years of age One parent with myopia (<−3 D in at least one eye)

Figure 2:
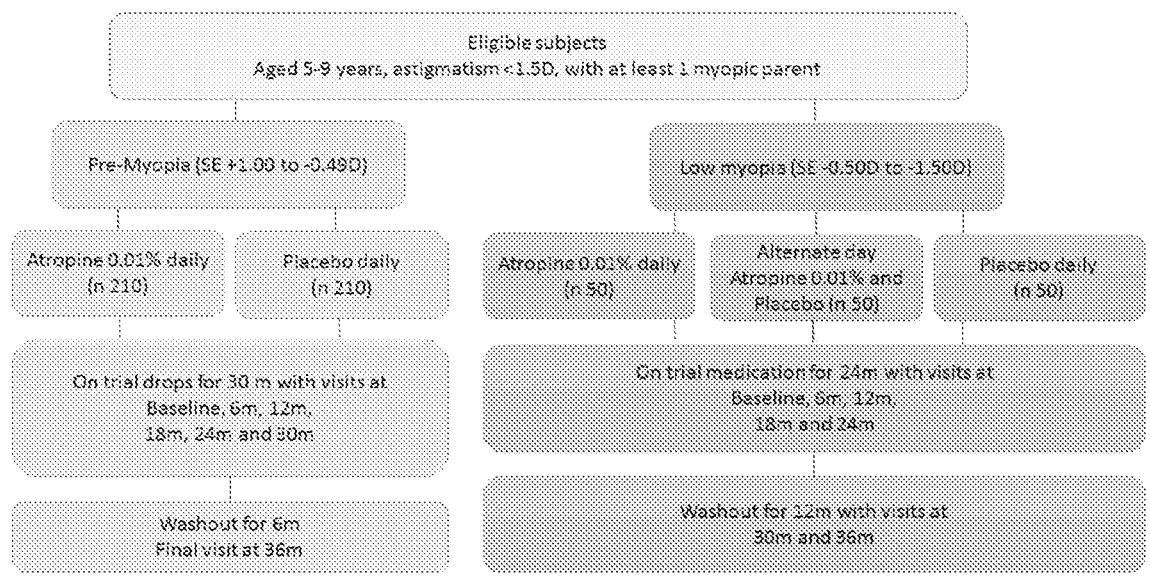
FIG. 2 is a schematic of a flow chart illustrating the study design of ATOM3.

Refractive error of spherical equivalent +1.00 D to −0.49 D (pre-myopic children), −0.50 D to −1.50 D (low-myopic children) as measured by cycloplegic autorefraction Astigmatism not more than 1.50 D as measured by cycloplegic or non-cycloplegic autorefraction Distance vision correctable to logMAR 0.2 or better in both eyes Normal intraocular pressure of not greater than 21 mmHg Normal ocular health other than myopia In good general health with no history of cardiac or significant respiratory diseases No regular use of asthma-requiring medications in the past one year as determined by investigator No allergy to atropine, cyclopentolate, proparacaine and benzalkonium chloride 1.4 Exclusion Criteria Children with ocular pathology or systemic diseases that may affect vision or refractive error Any ocular condition wherein topical atropine is contraindicated Previous use of atropine or pirenzepine Defective binocular function or stereopsis Amblyopia or manifest strabismus including intermittent tropia Any other conditions precluding adherence to the protocol including unwillingness to refrain from contact lens wear for the duration of the study 2. Study Design Design: Randomised Controlled, Double Blinded Study Participants: Eligible children, aged 5 to 9 years, 420 who are pre-myopic (SE +1.00 to −0.49 D) and 150 who have low myopia (SE −0.50 to −1.50 D). The pre-myopic children will be randomised to receive atropine 0.01% eye drops daily or placebo and the low myopic children will be randomised to receive either atropine 0.01% daily, atropine 0.01% every other day or placebo daily. See FIG. 2.

2.1 Randomization and Blinding

Randomization will be performed using an internet-based procedure hosted by Singapore Clinical Research Institute (SCRI). To minimize observation bias, this study is designed as a double-masked trial in which neither the study participants nor the investigators or optometrists responsible for measuring the study outcomes will be aware of the treatment given. To achieve this, the following steps will be followed:

Once the Consent Form signed and the child is deemed eligible, he/she will be assigned a study number that does not reveal the treatment assignment.

Treatment drops to be used from randomization at initial visit to Month-30 (for pre-myopes) and to Month-24 (for low-myopes) will be pre-labelled such that no one will be able to tell apart the treatment from the placebo eye drops.

In the low-myope group who have been randomized to receive every other day of atropine, the day on which atropine is instilled (odd or even) will also be randomized.

All investigators and study team (with the exception of the unmasked pharmacists or unmasked coordinator) will be masked to the type of treatment drops, as all drops to be used from randomization at initial visit to Month-30 (for pre-myopes) and to Month-24 (for low-myopes) will be pre-sorted and packaged in identical bottles before arriving in the clinic.

Parents or guardians are asked to seek advice only from the Clinic Coordinators or Coordinating Optometrist regarding matters pertaining to their child's treatment such as any unusual side effects.

Children will initially be seen by an investigative team where assessments will be performed. They will subsequently receive cycloplegic agents in both eyes before seeing the investigators or delegated optometrists involved in the measurement of the study outcomes.

These investigators or delegated optometrists will not perform any measurements that would offer a clue to the treatment given.

There will be four stratification groups based on the age of the subject. Each group will have a different series of trial numbers:

Pre-Myopes
Group One (Subjects aged 5 to 6 y)—Trial number will begin with 1001.
Group Two (Subjects, aged 7 to 9 y)—Trial numbers will begin with 2001.
Low-Myopes
Group Three (Subjects aged 5 to 6 y)—Trial number will begin with 3001.
Group Four (Subjects aged 7 to 9 y)—Trial numbers will begin with 4001.

An eligible child will be registered by the Coordinating Optometrist and assigned a trial number from the Registration List, depending on the stratification group the child belongs to (e.g. the first eligible subject (Pre-Myope) aged 5-6 y will belong to group one and be assigned trial number 1001, the next 1002 and so on). The assigned trial number will be recorded on the Registration Form.

| STUDY VISITS AND PROCEDURES | | | | | | | |
|---|---|---|---|---|---|---|---|
| | Baseline Visit | Month 6 | Month 12 | Month 18 | Month 24 | Month 30 | Month 36 |
| History or history update | x | x | x | x | x | x | x |
| Risk Factors Questionnaire | x | | | x | | | x |
| Lensometry (if applicable) | x | x | x | x | x | x | x |
| Presenting distance & near logMar VA (with current glasses if applicable) | x | x | x | x | x | x | x |
| Cover test | x | x | | | | | |
| Non-cycloplegic autorefraction | x | | | | | | |
| Non-cycloplegic autokeratometry | x | | | | | | |
| Non-cycloplegic subjective refraction (if presenting Distance VA > 0.2) | x | | | | | | |
| Non-cycloplegic BCVA distance logMAR (if presenting distance VA > 0.2) | x | | | | | | |
| Photopic pupil diameter | x | x | x | | x | | x |
| Amplitude of accommodation | x | x | x | | x | | x |
| Tonometry | x | x | x | | x | | |
| Instil topical anaesthetic and cycloplegic agents | x | x | x | x | x | x | x |
| Cycloplegic autorefraction | x | x | x | x | x | x | x |
| Cycloplegic autokeratometry | x | x | x | x | x | x | x |
| Cycloplegic subjective refraction | x | x | x | x | x | x | x |
| Cycloplegic BCVA distance logMAR | x | x | x | x | x | x | x |
| Slit-lamp examination | x | | x | | x | | x |
| Fundus photography | x | | x | | x | | x |
| IOL Master | x | x | x | x | x | x | x |
| Dispense trial medication | x | x | x | x | x (only pre-myope) | | |

2.2.1. Screening Visits and Procedures

At the first/recruitment visit, aims and design of the study will be explained to parents and children. Parent of children and children will be counselled regarding their rights and responsibilities and written informed consent will be obtained. Medical history (to exclude any known existing eye or systemic illness), drug allergy history (to exclude possible allergy to drops), and parental history of myopia will be obtained. Children will be screened for ocular pathology by assessing their distance and near logMar visual acuity, non-cycloplegic autorefraction/autokerametry, cover tests, measurement of photopic pupil size, amplitude of accommodation and tonometry. A non-cycloplegic subjective refraction with assessment of best corrected distance logMar VA will be performed if visual acuity with current glasses was >0.2.

If it is unlikely that the child will satisfy the inclusion/exclusion criteria of the study, parents will be informed, and no further tests will be done. If there is an ocular condition which may require further investigation, then parents of children will be advised to take their child to see an ophthalmologist.

Other baseline assessment tests such as cycloplegic autorefraction/autokeratometry, subjective refraction, slit lamp examination, fundus photography and IOL Master will be performed. Children will then be dispensed with trial medication.

At each return visit, parents and child will be asked about their use of eye drops and whether there have been any adverse events occurring within the past 6 months. Difficulties with accommodative function while performing near work and other activities, photophobia or sensitivity to light outdoors, and problems with daily activity will be identified. Diary of eye drop use and bottles of eye drops (both used and unused) will be collected.

History Review

At the first/recruitment visit, medical history (to exclude any known existing eye or systemic illness), drug allergy history (to exclude possible allergy to drops), and parental history of myopia will be obtained.

Risk Factors Questionnaire

On the first 18 Month or 36 months, parents will complete a myopia risk-factor assessment questionnaire which includes exposure to environmental (near work and outdoor activity) and familial risk factors (parental and sibling refractive status).

Lensometry

Lensometer will be used to assess current glasses prescription (if applicable).

Presenting Distance and Near Log MAR VA

Vision will be tested by optometrist using distance and near logMAR VA charts.

Cover Tests

Presence or absence of ocular alignment will be assessed by an optometrist using cover-uncover test for both distance and near at baseline and Month-6 visit.

Autorefraction and Autokeratometry

Autorefraction and autokeratometry will be tested with a table mounted autorefractor Canon RK at each visit. 5 refractive error measurements will be taken for each eye.

Subjective Refraction (Non-Cycloplegic/Cycloplegic)

A vision testing using combination of lenses that will provide the best corrected visual acuity (BCVA).

Photopic Pupil Size

Pupil size will be measured using the table mounted autorefractor Canon RK under photopic conditions (at 80 lux).

Amplitude of Accommodation

Amplitude of accommodation will be measured with a RAF rule.

Tonometry

Intraocular pressure will be measured with either a non-contact tonometer or contact tonometer such as the I-care device.

Cycloplegic Eye Drops

At each scheduled study visit, cycloplegia will be achieved using 1 drop of proparacaine 0.5%, followed by 3 drops of cyclopentolate 1% administered 5 minutes apart. Full cycloplegia is assumed to occur 30 minutes after last drop is administered.

Cycloplegic Autorefraction and Best Corrected Visual Acuity

Refractive errors will be measured at the baseline and subsequent follow-up visits by cycloplegic autorefraction, using a Canon RK autorefractor. Cycloplegic autorefraction was selected as the measure of refractive error because of its reliability, validity and objectivity, thus allowing for standardization of measurements over time.

At each visit, 5 refractive error measurements will be taken for each eye. For each of the 5 measures, the spherical equivalent will be calculated using the Thibos et al method, then the mean spherical equivalent will be calculated and used as a measure of progression of each eye.

Slit Lamp Examination

A slit lamp examination will be carried out by an ophthalmologist or a trained and delegated optometrist. Health of the surface of the eye, iris and lens will be assessed.

Fundus Photography

A fundus photograph of the posterior pole will be obtained at the baseline, and each yearly visit. Health of the optic nerve, macula and retina will be assessed at screening by a trained optometrist, and all photos will be reviewed by an ophthalmologist on the study team.

IOL Master

Non-contact partial interferometry will be used to measure the ocular axial length. This is performed using the Zeiss IOL Master which measures the length between the corneal vertex and retinal pigment epithelium along the visual axis using a red fixation beam with a resolution of 12 um and precision of 5 um. At each visit, 5 measures will be taken on each eye. The axial length measurement will be based on the average of 5 values when the maximum deviation between highest and lowest values in 0.05 mm or less. Other measures which will be recorded at the same time include anterior chamber depth and corneal curvatures.

2.2.2. Study Visits and Procedures

Baseline Visit

First/Screening examination (by Co-ordinating or Study Optometrist) are performed on a selected child with the following:

Lensometry (if applicable)
Presenting Distance and near logMar VA (with glasses if applicable)
Cover test at distance and near
Non-cycloplegic autorefraction and autokeratometry
Non-cycloplegic subjective refraction (if presenting distance logMar VA>0.2) and record best corrected distance VA
Photopic pupil diameter
Amplitude of accommodation
Tonometry If child still appears to be able to satisfy the inclusion/exclusion criteria of the study, Administer anaesthetic and cycloplegic eye drops Cycloplegic autorefraction and autokeratometry
Cycloplegic subjective refraction and best corrected distance cycloplegic logMar VA
Slit lamp examination
Fundus photography
IOL Master
Randomisation and Dispensing of Eye Drops
Once randomized, the study optometrist or co-ordinator will weigh and dispense the eye drops allocated to the child and provide verbal as well as written information to parents/guardians and child on the use of the eye drops.
Children in the Pre-myopic group will receive 1 box of 6-8 bottles (1 bottle to be used for one month).
Children in the Low myopic group will receive 2 boxes of 6-8 bottles (2 bottles for to be used for one month, to be used on alternate days).
Diary Chart
A six month diary chart will be provided to the parents/guardians of all subjects. Parents and children will be asked to check the boxes of the days as they administer the eye drops.
4.2.2.2 Follow-Up Visits (Month-6, 12, 18, 24 and 30 Visits)
Procedures
The Clinic co-ordinators will
Update history including review of any side-effects or problems with eye drops
Review compliance including questioning parents/guardians if they are aware of the type of treatment given to the child
Retrieve and weigh used bottles of eye drops and diary given out at past visit
Risk Factors Questionnaire? Pg 14. Listed on pg 13 on study visits and procedures table
The Co-ordinating Optometrist will
Update history (if not done by Clinic Co-ordinator)
Measure distance and near logMar VA (with glasses if applicable)
Perform lensometry (if applicable)
Perform cover test (at Month-6 visit)
Measure amplitude of accommodation (at Month-6, 12 and 24 visits)
Measure photopic pupil diameter (at Month-6, 12 and 24 visits)
Perform tonometry (at Month-6, 12 and 24 visits)
Administer the topical anaesthetic and cycloplegic agents
The Study Optometrist will
Perform cycloplegic autorefraction and autokeratometry
Perform cycloplegic subjective refraction
Measure best corrected cycloplegic logMAR distance visual acuity
Perform slit-lamp examination (at annual visits)
Obtain fundus photography (at annual visits)
Obtain biometry with IOL Master
Following the examination by the Study Optometrist, the Co-ordinating Optometrist will
Review all forms for completeness and accuracy
Provide child with letter for school and prescription for glasses if necessary
Replenish child's eye drops (except for pre-myopes at Month-30 visit and for low-myopes at Month-24 visit)
Arrange an appointment for next scheduled visit
For pre-myopes, children will stop eye drops from Month-30 onwards and undergo 6 months of washout. Washout is the observational time period after cessation of atropine when it is presumed there is no more drug present.

For low-myopes, children will stop eye drops from Month-24 onwards and undergo 12 months of washout.
4.2.2.5 Visit Range
All follow-up visits will be scheduled within a range of ±21 calendar days from the target date. All visits should fall within the window range for that specific visit.

| Visit | Target | Window Range |
|---|---|---|
| Baseline Visit (Time Zero) | Time 0 | NA |
| 6-Month Visit | 180 days from Time 0 | 159-201 Days |
| 1st Annual Visit | 360 days from Time 0 | 339-381 Days |
| 18-Month Visit | 540 days from Time 0 | 519-561 Days |
| 2nd Annual Visit | 720 days from Time 0 | 699-741 Days |
| 30-Month Visit | 900 days from Time 0 | 879-921 Days |
| $3^{rd}$ Annual Visit | 1,080 days from Time 0 | 1,059-1,101 Days |

2.2.3. Final Study Visit
Month-36 Visit/Exit Visit
The Clinic co-ordinators will
Update history
Risk Factors Questionnaire
The Co-ordinating Optometrist will
Update history (if not done by Clinic Co-ordinator)
Measure distance and near logMar VA (with glasses if applicable)
Perform lensometry (if applicable)
Measure photopic pupil diameter
Measure amplitude of accommodation
Administer the topical anaesthetic and cycloplegic agents
The Study Optometrist will:
Perform cycloplegic autorefraction and autokeratometry
Perform cycloplegic subjective refraction
Measure best corrected cycloplegic logMAR distance visual acuity
Perform slit-lamp examination
Obtain fundus photography
Obtain biometry with IOL Master
Following the examination by the Study Optometrist, the Co-ordinating Optometrist will
Review all forms for completeness and accuracy
Provide child with letter for school and prescription for glasses if necessary
2.3 Discontinuation/Withdrawal
2.3.1. Discontinuation Criteria
Early Stopping Rule
Pre-Myopia Children:
Early stopping may be considered if there is evidence or lack of, or strong evidence of efficacy, which makes unethical to continue with study.
Low-Myopia Children:
Consideration will be made for early stoppage if there is evidence of non-inferiority with the lower drug regimen.
It is anticipated that some subjects may experience adverse events or drug reactions as a result of the eye drops. In these circumstances, the subject may elect to stop treatment. The investigator may also decide to take the subject off the trial at any time if the investigator feels the subject's continued participation would impair his/her health. However, these subjects will be followed up with their outcomes for intention to treat analysis.
3. Trial Materials
Trial medication from baseline visit to 30-month visit will be formulated as:
0.01% Atropine
Active: Atropine Sulfate 0.01%

Vehicle: Hydroxypropyl Methylcellulose 1%
Preservative: Benzalkonium Chloride 1:10 000
Placebo
Active: None
Vehicle: Hydroxypropyl Methylcellulose 1%
Preservative: Benzalkonium Chloride 1:10 000

All trial medications will be manufactured by Xepa-Soul Pattinson (M) Sdn Bhd.

3.1 Trial Product(s)

The study drugs are clear, colorless sterile solution. The solutions are provided in 5 ml plastic dropper bottle. The study drug comes with active ingredient: Atropine Sulphate 0.01% w/v with preservative: Benzalkonium Chloride 0.01% w/v. The placebo comes with no active ingredient with preservative: Benzalkonium Chloride 0.01% w/v. Product insert for Atropine 0.01% is attached in Appendix 3.

3.2 Storage and Drug Accountability

The study drug comes with active ingredient: Atropine Sulphate 0.01% w/v with preservative: Benzalkonium Chloride 0.01% w/v. The placebo comes with no active ingredient with preservative: Benzalkonium Chloride 0.01% w/v. The solutions are provided in 5 ml plastic dropper bottle. The study drugs are stored below 30° C.

Being a double masked study, the study drugs to be used from baseline visit to Month-30 (for pre-myopes) and to Month-24 (for low-myopes) will be labelled only with trial number. The labelling will be done by an independent pharmacist. Each labelled bottle will either contain Atropine 0.01% or a placebo. The label on each bottle will include short study title, the designation of the eye drop bottle, the name and country of origin of the manufacturer, batch number, trial number, expiry date, dose frequency, storage conditions and the words "For Clinical Trial Use Only".

The labelled bottles will be dispensed at every scheduled visit from baseline visit to Month-24 visit (for pre-myopes) and to Month-18 visit (for low-myopes).

4. Treatment 4.1 Study Drug Formulations

Composition of Trial Medication
Trial medication will be formulated:
0.01% Atropine
Active: Atropine Sulfate 0.01%
Vehicle: Hydroxypropyl Methylcellulose 1%
Preservative: Benzalkonium Chloride 1:10 000
Placebo
Active: None
Vehicle: Hydroxypropyl Methylcellulose 1%
Preservative: Benzalkonium Chloride 1:10 000

4.2 Study Drug Administration

Pre myope group: Instil one drop to both eyes every night.

Low myope group: Instil one drop labelled as 'odd night' on odd days of the calendar to both eyes and instil one drop labelled as 'even night' on even days of the calendar to both eyes.

4.3 Specific Restrictions/Requirements

Subjects are to refrain from contact lens wear, as well as other treatment of myopia for the duration of the study.

Study drug may be stopped if subject has upper respiratory infections/fever and resumed when the adverse event resolves.

Study drug will be stopped in the event of any ocular inflammation, infection or injury until the adverse event resolves.

4.4 Blinding

Sealed emergency envelopes containing the randomized intervention of each subject will be given to the PI and keep in a secured cabinet at the Singapore Eye Research Institute. The instructions that the sealed code must only be opened in case of a medical emergency requiring the identification of the intervention must be clearly explained to designated staffs that have access to the envelope. If the sealed code for a particular subject is broken, the PI must document the reason(s) for breaking of the code and scan the completed envelope to SCM immediately. The original form must be given to the SCRI project coordinator subsequently.

5. Safety Measurements 5.1 Definitions

An adverse event (AE) is any untoward medical occurrence in a patient or clinical investigation subject administered a pharmaceutical product and which does not necessarily have a causal relationship with this treatment.

A serious adverse event (SAE) or reaction is any untoward medical occurrence that at any dose: results in death; is life-threatening; requires inpatient hospitalisation or prolongation of existing hospitalization; results in persistent or significant disability/incapacity; is a congenital anomaly/birth defect; is a medical event that may jeopardize the patient and may require medical or surgical intervention to prevent one of the outcomes listed above. All serious SAEs are reported.

6. Data Analysis

Data will be collected by trained and delegated team of ophthalmologists, optometrists, nurses and coordinators.

7. Sample Size and Statistical Methods 7.1 Determination of Sample Size

For pre-myopic group of study participants:

Incidence estimate: data from 2 schools in SCORM showed 43% myopia incidence over 3 years (Saw et al, IOVS 2005). Based on spherical equivalent changes roughly linearly in SCORM (Wong et al., IOVS 2010), 2.5-year incidence is estimated as 2.5/3 of 43%, or about 35%. This should be a conservative estimate (under-estimate) of the incidence without intervention, as the target age group (5-9 years) is younger than SCORM (7-9 years) and incidence is higher in the younger ages.

Effect size estimate: comparing placebo control and 0.01% atropine in ATOM1 and ATOM2 (Chia et al., Ophth 2011), risk ratio of myopia progression by over 0.5 D decline over 2 years is about 0.6.

Sample size: assuming effect size of risk ratio=0.6, control incidence=35%, n=175 per group is needed for 80% power and 5% 2-sided type 1 error rate. Assuming 15% loss to follow-up (ATOM2 loss to follow-up was 11%), a sample size of about 210 per group is needed. Total sample size (two groups combined) is 420.

For Low-Myopic Group of Study Participants

Correlation arising from two eyes per child: ATOM2 data showed a high degree of design effect (1.74) arising from correlation between the SE in two eyes of the same child (Chia et al. Opht 2011). The analysis of two eyes per child is therefore only slightly more informative than the analysis of one randomly selected eye per child. For sample size planning purpose, we conservatively assumed that there is only one eye's worth of information per child.

Estimate of mean and SD of change in SE: SCORM data (Saw et al. IOVS 2005) showed that, among low myopia (−3 D to −0.5 D) the mean 2-year change in SE was approximately −1.6 D. The SD was approximately 0.67.

Effect size estimate: In ATOM1 and ATOM2, mean 2-year decline in SE was about −1.2 D in placebo and −0.5 D in 0.01% atropine daily (Chia et al. Opht 2011), i.e. about 58% reduction. Atropine 0.01% every-other-day and atropine 0.01% daily can reduce the mean change in SE by at least 30% (i.e. 30% of 1.6 D=0.48 D).

Sample size: Based on the above parameters, for 90% power and 2-sided 5% test, at least 41 participants were needed per arm to demonstrate the primary aim on efficacy of Atropine 0.01% daily and Atropine 0.01% every-other-day as compared to placebo controls. We will recruit 50 low myopic children for each of the three study arms, leading to a total sample size of 150. This allows for about 15% drop-outs.

7.2 Statistical and Analytical Plans

All statistical analyses were based on the intention-to-treat principle.

In the prevention trial, proportions of pre-myopic participants positive for primary endpoint (SE<−0.5 D) and secondary endpoint (SE<−1.5 D or wear glasses) at 2.5 years in each group will be estimated with 95% confidence interval (CI). Difference in proportions and its 95% CI will be estimated by the generalized linear model with binomial distribution and identity link function.

In the low-myopia trial, data from both eyes will be analyzed together, using the robust standard errors for cluster data for inference. Mean change in SE from baseline to 2 years will be compared between the 3 groups of low-myopic participants and between each atropine group versus placebo group using generalized linear model with Gaussian distribution, identify link function and the wald test. Difference in mean change in SE between every-other-day and daily atropine groups (daily minus every-other-day) and its 90% CI will be estimated.

REFERENCES

1. Barathi V A, Beuerman R W. Molecular mechanisms of muscarinic receptors in mouse scleral fibroblasts: Prior to and after induction of experimental myopia with atropine treatment. Mol Vis. 2011 Mar. 9; 17:680-92.
2. Barathi V A, Kwan J L, Tan Q S, Weon S R, Seet L F, Goh L K, Vithana E N, Beuerman R W. Muscarinic cholinergic receptor (M2) plays a crucial role in the development of myopia in mice. Dis Model Mech. 2013 September; 6(5):1146-58.
3. Dirani M, Chan Y H, Gazzard G, et al. Prevalence of refractive error in Singaporean Chinese children: the Strabismus, Amblyopia and Refractive Error in young Singaporean Children (STARS) Study. Invest Ophthalmol Vis Sci 2010; 51:1348-55.
4. Saw S M, Tong L, Chua W H, et al. Incidence and progression of myopia in Singaporean school children. Invest Ophthalmol Vis Sci 2005; 45:51-7.
5. Wu H M, Seet B, Yap E P, et al. Does education explain ethnic difference in myopia prevalence? A population-based study of young adult males in Singapore. Optom Visc Sci 2001; 78:234-9.
6. Chang L, Pan C W, Ohno-Matsui K, Lin X, Cheung G C, Gazzard G, Koh V, Hamzah H, Tai E S, Lim S C, Mitchell P, Young T L, Aung T, Wong T Y, Saw S M. Myopia-related fundus changes in singapore adults with high myopia. Am J Ophthalmol 2013; 155(6):991-999.
7. Chua W H, Balakrishnan V, Chan Y H, et al. Atropine for the treatment of childhood myopia. Ophthalmology 2006; 113:2285-91.
8. Tong L, Huang X L, Koh A L, et al. Atropine for the treatment of childhood myopia: effect on myopia progression after cessation of atropine. Ophthalmology 2009; 116:572-9.
9. Chia A, Chua W H, Cheung Y B, Wong W L, Lingham A, Fong A, Tan D. Atropine for the treatment of childhood myopia: safety and efficacy of 0.5%, 0.1%, and 0.01% doses (Atropine for the Treatment of Myopia 2). Ophthalmology 2012; 119(2):347-54.
10. Chia A, Chua W H, Wen L, Fong A, Goon Y Y, Tan D. Atropine for the treatment of childhood myopia: changes after stopping atropine 0.01%, 0.1% and 0.5%. Am J Ophthalmol 2014:157(2):451-457.
11. Gimbel H V. The control of myopia with atropine. Can J Ophthalmol 1973; 8:527-32.
12. Bedrossian R H. The effects of atropine on myopia. Ophthalmology 1979; 86:713-7.
13. Brodstein R S, Brodstein D E, Olson R J, et al. The treatment of myopia with atropine and bifocals: a long-term prospective study. Ophthalmology 1984; 91:1373-9.
14. Brenner R L. Further observations on use of atropine in the treatment of myopia. Ann Ophthalmol 1985; 17:137-40.
15. Chou A C, Shih Y F, Ho T C, Lin L L. The effectiveness of 0.5% atropine in controlling high myopia in children. J Ocul Pharmacol Ther 1997; 13:61-7.
16. Romano P E, Donovan J P. Management of progressive school myopia with topical atropine eye drops and photochromic bifocal spectacles. Binocul Vis Strabismus Q 2000; 15:257-60.
17. Kennedy R H, Dyer J A, Kennedy M A, et al. Reducing the progression of myopia with atropine: a long term cohort study of Olmsted County students. Binocul Vis Strabismus Q 2000; 15(suppl):281-304.
18. Chiang M F, Kouzis A, Pointer R W, Repka M X. Treatment of childhood myopia with atropine eye drops and bifocal spectacles. Binocul Vis Strabismus Q 2001; 16:209-15.
19. Syniuta L A, Isenberg S J. Atropine and bifocals can slow the progression of myopia in children. Binocul Vis Strabismus Q 2001; 16:203-8.
20. Lee J J, Fang P C, Yang I H, et al. Prevention of myopia progression with 0.05% atropine solution. J Ocul Pharmacol Ther 2006; 22:41-6.
21. Fan D S, Lam D S, Chan C K, et al. Topical atropine in retarding myopic progression and axial length growth in children with moderate to severe myopia: a pilot study. Jpn J Ophthalmol 2007; 51:27-33.
22. Yen M Y, Liu J H, Kao S C, Shiao C H. Comparison of the effect of atropine and cyclopentolate on myopia. Ann Ophthalmol 1989; 21:180-2, 187.
23. Shih Y F, Chen C H, Chou A C, et al. Effects of different concentrations of atropine on controlling myopia in myopic children. J Ocul Pharmacol Ther 1999; 15:85-90.
24. Shih Y F, Hsiao C K, Chen C J, et al. An intervention trial on efficacy of atropine and multi-focal glasses in controlling myopic progression. Acta Ophthalmol Scand 2001; 79:233-6.
25. Liang C K, Ho T Y, Li T C, et al. A combined therapy using stimulating auricular acupoints enhances lower-level atropine eye drops when used for myopia control in school-aged children evaluated by a pilot randomized controlled clinical trial. Complement Ther Med 2008; 16:305-10.
26. Fang P C, Chung M Y, Yu H J, Wu P C. Prevention of myopia onset with 0.025% atropine in premyopic children. J Ocul Pharmacol Ther 2010; 26:341-5.
27. Wu P C, Yang Y H, Fang P C. The long-term results of using low-concentration atropine eye drops for controlling myopia progression in schoolchildren. J Ocul Pharmacol Ther 201; 27(5):461-6.
28. Loh K L, Lu Q, Tan D, Chia A. Risk factors for progressive myopia in the atropine therapy for myopia study. Am J Ophthalmo 015 May; 159(5):945-9.

29. Wong H B, Machin D, Tan S B, Wong T Y, Saw S M. Ocular component growth curves amongst Singapore children with different refractive error status. Invest Ophthalmol Vis Sci 2010; 51: 1341-7.
30. Chia A, Chua W H, Tan D. Effect of topical atropine on astigmatism. Br J Ophthalmol. 2009 June; 93(6):799-802.
31. Luu C D, Lau A M, Koh A H, Tan D. Multifocal electroretinogram in children on atropine treatment for myopia. Br J Ophthalmol. 2005 February; 89(2):151-3.
32. Chang L, Pan C W, Ohno-Matsui K, Lin X, Cheung G C, Gazzard G, Koh V, Hamzah H, Tai E S, Lim S C, Mitchell P, Young T L, Aung T, Wong T Y, Saw S M. Myopia-related fundus changes in Singapore adults with high myopia. Am J Ophthalmol. 2013, June; 155(6):991-999.
33. Chia A, Li W, Tan D, Luu C D. Full-field electroretinogram findings in children in the atropine treatment for myopia (ATOM2) study. Doc Ophthalmol. 2013 Jan. 5.
34. Fang P C, Chung M Y, Yu H J, Wu P C. Prevention of myopia onset with 0.025% atropine in premyopic children. J Oculo Pharmacol Ther. 2010 August: 26(4):341-5.
35. Cheng D, Woo G C, Drobe B, Schmid K L. Effect of bifocal and prismatic bifocal spectacles on myopia progression in children: three-year results of a randomized clinical trial. JAMA Opthalmo 2014 March: 132(3):258-64.
36. Barr J T, Rah M J, Jackson J M, Jones L A. Orthokeratology and corneal refractive therapy: a review and recent findings. Eye Contact Lens 2003 January: 29:49-53.
37. Walline J, Rah M J, Jones L A. The Children's Overnight Orthokeratology Investigation (COOKI) pilot study. Optom Vis Sci 2004 June: 81(6):407-13.
38. Walline J J[1], Lindsley K, Vedula S S, Cotter S A, Mutti D O, Twelker J D. Interventions to slow progression of myopia in children. Cochrane Database Syst Rev. 2011 December: 7(12).
36. Goldschmidt E. Ocular morbidity in myopia. Acta Ophthalmol 1988; 185:86-7.
37. Saw S M, Gazzard G, Shih-Yen E C, Chua W H. Myopia and associated pathological complications. Ophthalmic Physiol Opt. 2005 September; 25(5):381-91.
38. Chen S J, Cheng C Y, Li A F, Peng K L, Chou P, Chiou S H, Hsu W M. Prevalence and associated risk factors of myopic maculopathy in elderly Chinese: the Shihpai eye study. Invest Ophthalmol Vis Sci. 2012 Jul. 24; 53(8): 4868-73.
39. Alimanović-Halilović E. Correlation between refraction level and retinal breaks in myopic eye. Bosn J Basic Med Sci. 2008 November; 8(4):346-9.
40. Chen L, Wang K, Esmaili D D, Xu G. Rhegmatogenous retinal detachment due to paravascular linear retinal breaks over patchy chorioretinal atrophy in pathologic myopia. Arch Ophthalmol. 2010 December; 128(12):1551-4.
41. Bansal A S, Hubbard G B 3rd. Peripheral retinal findings in highly myopic children < or =10 years of age. Retina. 2010 April; 30(4 Suppl):S15-9.
42. Wu W C, Lai C C, See L C, Tsao Y P, Yang K J, Chen T L. Unambiguous comparison of juvenile and senile rhegmatogenous retinal detachment. Ophthalmic Surg Lasers Imaging. 2005 May-June; 36(3):197-204.
44. Chou S C, Yang C H, Lee C H, Yang C M, Ho T C, Huang J S, Lin C P, Chen M S, Shih Y F. Characteristics of primary rhegmatogenous retinal detachment in Taiwan. Eye (Lond). 2007 August; 21(8):1056-61.
45. Jamil M H, Farooq N, Khan M T, Jamil A Z. Characteristics and pattern of rhegmatogenous retinal detachment in pakistan. J Coll Physicians Surg Pak. 2012 August; 22(8): 501-4.
46. Nagpal M, Nagpal K, Rishi P, Nagpal P N. Juvenile rhegmatogenous retinal detachment. Indian J Ophthalmol. 2004 December; 52(4):297-302.
47. Wang N K, Tsai C H, Chen Y P, Yeung L, Wu W C, Chen T L, Lin K K, Lai C C. Pediatric rhegmatogenous retinal detachment in East Asians. Ophthalmology. 2005 November; 112(11):1890-5.
48. Chang P Y, Yang C M, Yang C H, Huang J S, Ho T C, Lin C P, Chen M S, Chen L J, Wang J Y. Clinical characteristics and surgical outcomes of pediatric rhegmatogenous retinal detachment in Taiwan. Am J Ophthalmol. 2005 June; 139(6):1067-72.
49. Chen S N, Jiunn-Feng H, Te-Cheng Y. Pediatric rhegmatogenous retinal detachment in taiwan. Retina. 2006 April; 26(4):410-4.
50. Sheu S J, Ger L P, Chen J F. Axial myopia is an extremely significant risk factor for young-aged pseudophakic retinal detachment in taiwan. Retina. 2006 March; 26(3):322-7.
51. Lee R W, Mayer E J, Markham R H. The aetiology of paediatric rhegmatogenous retinal detachment: 15 years experience. Eye (Lond). 2008 May; 22(5):636-40.
52. Wang N K, Chen Y P, Lai C C, Chen T L, Yang K J, Kuo Y H, Chao A N, Wu W C, Chen K J, Hwang Y S, Yeung L, Liu L. Paediatric retinal detachment: comparison of high myopia and extreme myopia. Br J Ophthalmol. 2009 May; 93(5):650-5.
53. Soheilian M, Ramezani A, Malihi M, Yaseri M, Ahmadieh H, Dehghan M H, Azarmina M, Moradian S, Peyman G A. Clinical features and surgical outcomes of pediatric rhegmatogenous retinal detachment. Retina. 2009 April; 29(4):545-51.
54. Mitry D, Charteris D G, Fleck B W, Campbell H, Singh J. The epidemiology of rhegmatogenous retinal detachment: geographical variation and clinical associations. Br J Ophthalmol. 2010 June; 94(6):678-84.
55. Lee S Y, Ong S G, Wong D W, Ang C L. Giant retinal tear management: an Asian experience. Eye (Lond). 2009 March; 23(3):601-5.
56. Mehdizadeh M, Afarid M, Haqiqi M S. Risk factors for giant retinal tears. J Ophthalmic Vis Res. 2010; 5(4):246-9.
57. Faghihi H, Jalali K H, Amini A, Hashemi H, Fotouhi A, Esfahani M R. Rhegmatogenous retinal detachment after LASIK for myopia. J Refract Surg. 2006 May; 22(5):448-52.
58. Lee S Y, Ong S G, Yeo K T, Wong D W, Ang C L. Retinal detachment after laser refractive surgery at the Singapore National Eye Centre. J Cataract Refract Surg. 2006 March; 32(3):536-8.
59. Qin B, Huang L, Zeng J, Hu J. Retinal detachment after laser in situ keratomileusis in myopic eyes. Am J Ophthalmol. 2007 December; 144(6):921-923.
60. Erie J C, Raecker M E, Baratz K H, Schleck C D, Robertson D M. Risk of retinal detachment after cataract extraction, 1980-2004: a population-based study. Trans Am Ophthalmol Soc. 2006; 104:167-75.
61. Alio J L, Ruiz-Moreno J M, Shabayek M H, Lugo F L, Abd El Rahman A M. The risk of retinal detachment in high myopia after small incision coaxial phacoemulsification. Am J Ophthalmol. 2007 July; 144(1):93-98.
62. Williams M A, McGimpsey S, Abugreen S, Chan W, Sharkey J A, Best R M, Johnston P B. The incidence and rate of rhegmatogenous retinal detachment seven years after cataract surgery in patients with high myopia. Ulster Med J. 2009 May; 78(2):99-104.
63. Jiang T, Chang Q, Wang X, Huang X. Retinal detachment after phakic intraocular lens implantation in severe myopic eyes. Graefes Arch Clin Exp Ophthalmol. 2012 Apr. 4. [Epub ahead of print]
64. Feng L G, Jin X H, Li J K, Zhai J, Fang W, Mo J F, Feng Q R, Li Y M. Surgical management of retinal detachment resulting from macular hole in a setting of high myopia. Yan Ke Xue Bao. 2012 June; 27(2):69-75.
65. Nakanishi H, Kuriyama S, Saito I, Okada M, Kita M, Kurimoto Y, Kimura H, Takagi H, Yoshimura N. Prognostic factor analysis in pars plana vitrectomy forretinal detachment attributable to macular hole in high myopia: a multicenterstudy. Am J Ophthalmol. 2008 August; 146(2):198-204.
66. Gonzales C R, Gupta A, Schwartz S D, Kreiger A E. The fellow eye of patients with phakic rhegmatogenous retinal detachment from atrophic holes of lattice degeneration without posterior vitreous detachment. Br J Ophthalmol. 2004 November; 88(11):1400-2.
67. Oie Y, Emi K. Incidence of fellow eye retinal detachment resulting from macular hole. Am J Ophthalmol. 2007 February; 143(2):203-205.
68. Ripandelli G, Coppé A M, Parisi V, Stirpe M. Fellow eye findings of highly myopic subjects operated for retinal detachment associated with a macular hole. Ophthalmology. 2008 September; 115(9):1489-93.
69. Mitry D, Singh J, Yorston D, Siddiqui M A, Murphy A L, Wright A F, Fleck B W, Campbell H, Charteris D G. The fellow eye in retinal detachment: findings from the Scottish Retinal Detachment Study. Br J Ophthalmol. 2012 January; 96(1):110-3.
70. Bottoni F, Tilanus M. The natural history of juxtafoveal and subfoveal choroidal neovascularization in high myopia. Int Ophthalmol. 2001; 24(5):249-55.
71. Ohno-Matsui K, Yoshida T. Myopic choroidal neovascularization: natural course and treatment. Curr Opin Ophthalmol. 2004 June; 15(3):197-202.
72. Shih Y F, Ho T C, Hsiao C K, Lin L L. Visual outcomes for high myopic patients with or without myopic maculopathy: a 10 year follow up study. Br J Ophthalmol. 2006 May; 90(5):546-50.
73. Hayashi K, Ohno-Matsui K, Shimada N, Moriyama M, Kojima A, Hayashi W, Yasuzumi K, Nagaoka N, Saka N, Yoshida T, Tokoro T, Mochizuki M. Long-term pattern of progression of myopic maculopathy: a natural history study. Ophthalmology. 2010 August; 117(8):1595-611.
74. Silva R. Myopic maculopathy: a review. Ophthalmologica. 2012; 228(4):197-213.
75. Kobayashi K, Ohno-Matsui K, Kojima A, Shimada N, Yasuzumi K, Yoshida T, Futagami S, Tokoro T, Mochizuki M. Fundus characteristics of high myopia in children. Jpn J Ophthalmol. 2005 July-August; 49(4):306-11.
76. Shimada N, Ohno-Matsui K, Baba T, Futagami S, Tokoro T, Mochizuki M. Natural course of macular retinoschisis in highly myopic eyes without macular hole or retinal detachment. Am J Ophthalmol. 2006 September; 142(3):497-500.
77. Shimada N, Ohno-Matsui K, Yoshida T, Sugamoto Y, Tokoro T, Mochizuki M. Progression from macular retinoschisis to retinal detachment in highly myopic eyes is associated with outer lamellar hole formation. Br J Ophthalmol. 2008 June; 92(6):762-4.
78. Wu P C, Chen Y J, Chen Y H, Chen C H, Shin S J, Tsai C L, Kuo H K. Factors associated with foveoschisis and foveal detachment without macular hole in high myopia. Eye (Lond). 2009 February; 23(2):356-61.
79. Faghihi H, Hajizadeh F, Riazi-Esfahani M. Optical coherence tomographic findings in highly myopic eyes. J Ophthalmic Vis Res. 2010 April; 5(2):110-21.
80. Fujimoto M, Hangai M, Suda K, Yoshimura N. Features associated with foveal retinal detachment in myopic macular retinoschisis. Am J Ophthalmol. 2010 December; 150(6):863-70.
81. Sun C B, Liu Z, Xue A Q, Yao K. Natural evolution from macular retinoschisis to full-thickness macular hole in highly myopic eyes. Eye (Lond). 2010 December; 24(12): 1787-91.
82. Jonas J B, Decker A, Mangler B, Schlichtenbrede F C. Macular holes and central retinal detachment. Acta Ophthalmol. 2011 June; 89(4):e377-8.
83. Liu H Y, Zou H D, Liu K, Song Z Y, Xu X, Sun X D. Posterior vitreous cortex contributes to macular hole in highly myopic eyes with retinal detachment. Chin Med J (Engl). 2011 August; 124(16):2474-9.
84. Jo Y, Ikuno Y, Nishida K. Retinoschisis: a predictive factor in vitrectomy for macular holes without retinal detachment in highly myopic eyes. Br J Ophthalmol. 2012 February; 96(2):197-200.
85. Ikuno Y, Sayanagi K, Soga K, Sawa M, Gomi F, Tsujikawa M, Tano Y. Lacquer crack formation and choroidal neovascularization in pathologic myopia. Retina. 2008 October; 28(8):1124-31.
86. Ikuno Y, Jo Y, Hamasaki T, Tano Y. Ocular risk factors for choroidal neovascularization in pathologic myopia. Invest Ophthalmol Vis Sci. 2010 July; 51(7):3721-5.
87. Y M, Yoon J U, Koh H J. The analysis of lacquer crack in the assessment of myopic choroidal neovascularization. Eye (Lond). 2011 July; 25(7):937-46.
88. Neelam K, Cheung C M, Ohno-Matsui K, Lai T Y, Wong T Y. Choroidal neovascularization in pathological myopia. Prog Retin Eye Res. 2012 September; 31(5):495-525.
89. Yoshida T, Ohno-Matsui K, Yasuzumi K, Kojima A, Shimada N, Futagami S, Tokoro T, Mochizuki M. Myopic choroidal neovascularization: a 10-year follow-up. Ophthalmology. 2003 July; 110(7):1297-305.
90. Miller D G, Singerman L J. Vision loss in younger patients: a review of choroidal neovascularization. Optom Vis Sci. 2006 May; 83(5):316-25.
91. Soubrane G. Choroidal neovascularization in pathologic myopia: recent developments in diagnosis and treatment. Surv Ophthalmol. 2008 March-April; 53(2):121-38.
92. Montero J A, Ruiz-Moreno J M. Treatment of choroidal neovascularization in high myopia. Curr Drug Targets. 2010 May; 11(5):630-44.
93. Mitry D, Zambarakji H. Recent trends in the management of maculopathy secondary to pathological myopia. Graefes Arch Clin Exp Ophthalmol. 2012 January; 250(1):3-13.
94. Nadal J, Verdaguer P, Canut M I. Treatment of retinal detachment secondary to macular hole in high myopia: vitrectomy with dissection of the inner limiting membrane to the edge of the staphyloma and long-term tamponade. Retina. 2012 September; 32(8):1525-30.
95. Wu T T, Kung Y H. Comparison of anatomical and visual outcomes of macular hole surgery in patients with high myopia vs. non-high myopia: a case-control study using optical coherence tomography. Graefes Arch Clin Exp Ophthalmol. 2012 March; 250(3):327-31.
96. Qu J, Zhao M, Jiang Y, Li X. Vitrectomy outcomes in eyes with high myopic macular hole without retinal detachment. Retina. 2012 February; 32(2):275-80.

97. Soheilian M, Ghaseminejad A K, Yazdani S, Ahmadieh H, Azarmina M, Dehghan M H, Moradian S, Anisian A, Peyman G A. Surgical management of retinal detachment in highly myopic eyes with macular hole. Ophthalmic Surg Lasers Imaging. 2007 January-February; 38(1):15-22.
98. Chen Y P, Chen T L, Yang K R, Lee W H, Kuo Y H, Chao A N, Wu W C, Chen K J, Lai C C. Treatment of retinal detachment resulting from posterior staphyloma-associated macular hole in highly myopic eyes. Retina. 2006 January; 26(1):25-31.
99. Chen H, Wen F, Li H, Zuo C, Zhang X, Huang S, Luo G. The types and severity of high myopic maculopathy in Chinese patients. Ophthalmic Physiol Opt. 2012 January; 32(1):60-7.
100. Pruett R C. Complications associated with posterior staphyloma. Curr Opin Ophthalmol. 1998 June; 9(3):16-22.
101. Ohno-Matsui K, Akiba M, Moriyama M, Ishibashi T, Hirakata A, Tokoro T. Intrachoroidal cavitation in macular area of eyes with pathologic myopia. Am J Ophthalmol. 2012 August; 154(2):382-93.
102. Carbonelli M, Savini G, Zanini M, Barboni P. Peripapillary detachment in pathologic myopia: Unusual OCT findings. Clin Ophthalmol. 2007 September; 1(3):327-9.
103. Shimada N, Ohno-Matsui K, Iwanaga Y, Tokoro T, Mochizuki M. Macular retinal detachment associated with peripapillary detachment in pathologic myopia. Int Ophthalmol. 2009 April; 29(2):99-102.
104. Jonas J B, Jonas S B, Jonas R A, Holbach L, Panda-Jonas S. Histology of the parapapillary region in high myopia. Am J Ophthalmol. 2011 December; 152(6):1021-9.
105. Park H Y, Lee K, Park C K. Optic disc torsion direction predicts the location of glaucomatous damage in normal-tension glaucoma patients with myopia. Ophthalmology. 2012 September; 119(9):1844-51.
106. Hayashi K, Tomidokoro A, Lee K Y, Konno S, Saito H, Mayama C, Aihara M, Iwase A, Araie M. Spectral-domain optical coherence tomography of β-zone peripapillary atrophy: influence of myopia and glaucoma. Invest Ophthalmol Vis Sci. 2012 Mar. 21; 53(3):1499-505.
107. Samarawickrama C, Mitchell P, Tong L, Gazzard G, Lim L, Wong T Y, Saw S M. Myopia-related optic disc and retinal changes in adolescent children from singapore. Ophthalmology. 2011 October; 118(10):2050-7.
108. Xu L, Wang Y, Wang S, Wang Y, Jonas J B. High myopia and glaucoma susceptibility the Beijing Eye Study. Ophthalmology. 2007 February; 114(2):216-20.
109. Kuzin A A, Varma R, Reddy H S, Torres M, Azen S P; Los Angeles Latino Eye Study Group. Ocular biometry and open-angle glaucoma: the Los Angeles Latino Eye Study. Ophthalmology. 2010 September; 117(9):1713-9.
110. Perera S A, Wong T Y, Tay W T, Foster P J, Saw S M, Aung T. Refractive error, axialdimensions, and primary open-angle glaucoma: the Singapore Malay Eye Study. Arch Ophthalmol. 2010 July; 128(7):900-5. PubMed PMID: 20625053.
111. Marcus M W, de Vries M M, Junoy Montolio F G, Jansonius N M. Myopia as a risk factor for open-angle glaucoma: a systematic review and meta-analysis. Ophthalmology. 2011 October; 118(10):1989-1994.
112. Liang Y B, Friedman D S, Zhou Q, Yang X, Sun L P, Guo L X, Tao Q S, Chang D S, Wang N L; Handan Eye Study Group. Prevalence of primary open angle glaucoma in a rural adult Chinese population: the Handan eye study. Invest Ophthalmol Vis Sci. 2011 Oct. 21; 52(11):8250-7.
113. Pan C W, Cheung C Y, Aung T, Cheung C M, Zheng Y F, Wu R Y, Mitchell P, Lavanya R, Baskaran M, Wang J J, Wong T Y, Saw S M. Differential Associations of Myopia with Major Age-related Eye Diseases: The Singapore Indian Eye Study. Ophthalmology. 2012 Oct. 17.
114. Yang Y, Li Z, Wang N, Wu L, Zhen Y, Wang T, Ren C, Peng X, Hao J, Xia Y. Intraocular Pressure Fluctuation in Patients With Primary Open-angle Glaucoma Combined With High Myopia. J Glaucoma. 2012 Jun. 4.
115. Rosman M, Zheng Y, Lamoureux E, Saw S M, Aung T, Tay W T, Wang J J, Mitchell P, Tai E S, Wong T Y. Review of key findings from the Singapore Malay Eye Study (SiMES-1). Singapore Med J. 2012 February; 53(2):82-7.
116. Chua S Y, Ikram M K, Tan C S, Lee Y S, Ni Y, Shirong C, Gluckman P D, Chong Y S, Yap F, Wong T Y, Ngo C S, Saw S M; Growing Up in Singapore Towards Healthy Outcomes Study Group. Relative Contribution of Risk Factors for Early-Onset Myopia in Young Asian Children. Invest Ophthalmol Vis Sci. 2015 December; 56(13):8101-7.
117. Huang J, Wen D, Wang Q, McAlinden C, Flitcroft I, Chen H, Saw S M, Chen H, Bao F, Zhao Y, Hu L, Li X, Gao R, Lu W, Du Y, Jinag Z, Yu A, Lian H, Jiang Q, Yu Y, Qu J. Efficacy Comparison of 16 Interventions for Myopia Control in Children: A Network Meta-analysis. Ophthalmology. 2016 April; 123(4):697-708.
118. Walline J J (1), Lindsley K, Vedula S S, Cotter S A, Mutti D O, Twelker J D. Interventions to slow progression of myopia in children. Cochrane Database Syst Rev. 2011 Dec. 7; (12):CD004916.
119. Schaeffel F, Burkhardt E, Howland H C, Williams R W. Measurement of refractive state and deprivation myopia in two strains of mice. Optom Vis Sci. 2004; 81:99-110.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

What is claimed is:

1. A method for preventing or delaying the onset of myopia comprising administering to a subject in an eye a composition comprising from about 0.001% to less than 0.025% atropine, wherein the Spherical Equivalent (SE) of the eye is a positive value or a negative value less than —0.5D before administration of the composition.

2. The method of claim 1, wherein the atropine is present in the form of atropine salt.

3. The method of claim 2, wherein the atropine salt is atropine sulfate or atropine acetate.

4. The method of claim 1, wherein the composition comprises about 0.01% atropine.

5. The method of claim 1, wherein the composition comprises about 0.001% to 0.0249% atropine.

6. The method of claim 1, wherein the composition is administered every other day, or at least once daily, or at least twice daily.

7. The method of claim 1, wherein each administration is performed by instilling at least one drop, at least two drops, or at least three drops to the eye, wherein each drop contains about 20-100 microliter liquid.

8. The method of claim 1, wherein the administration continues for the period of at least six months, one year, two years, three years, four years, five years, six years, seven years, ten years or longer.

9. The method of claim 1, wherein the composition further comprises at least one pharmaceutically acceptable excipient.

10. The method of claim 1, wherein the at least one pharmaceutically acceptable excipient is selected from the group consisting of benzalkonium chloride and hydroxypropyl methylcellulose.

11. The method of claim 10, wherein the benzalkonium chloride is present in the composition at a concentration of about 0.01% or wherein the hydroxypropyl methylcellulose is present in the composition at a concentration of about 1%.

12. The method of claim 1, wherein the composition contains no preservatives.

13. The method of claim 1, wherein the subject is at least 5 years old.

14. The method according to claim 1, wherein the Spherical Equivalent (SE) of the eye is within the range of from +1.00D to −0.49D before administration of the composition.

15. The method of claim 1, wherein the subject has no astigmatism or has astigmatism of not more than 1.50D as measured by cycloplegic or non-cycloplegic autorefraction before administration of the composition, or wherein the pupil of the eye has no dilation or a dilation of no greater than 0.2 mm during the period of administration of the composition, or wherein the eye has no loss of accommodation or a loss of accommodation of no greater than 9D.

16. The method of claim 1, wherein the subject has at least one myopic parent.

17. The method of claim 1, wherein the onset of myopia is delayed for greater than 6 months, 12 months, 18 months, two years, three years, five years, six years, eight years, or longer.

18. The composition of claim 5, wherein the composition comprises about 0.001%, about 0.002%, about 0.003%, about 0.004%, about 0.005%, about 0.006%, about 0.007%, about 0.008%, about 0.009%, about 0.01%, about 0.011%, about 0.012%, about 0.013%, about 0.014%, about 0.015%, about 0.016%, about 0.017%, about 0.018%, about 0.019%, about 0.02%, about 0.021%, about 0.022%, about 0.023%, about 0.024%, about 0.0245% or about 0.0249% atropine.

19. The method of claim 14, wherein the SE is measured by Autorefractor after administration of cycloplegia.

20. The method of claim 13, wherein the subject is between 5 and 9 years old.

* * * * *